United States Patent
Gauthier et al.

(10) Patent No.: US 7,301,131 B2
(45) Date of Patent: Nov. 27, 2007

(54) MICROWAVE ABLATION INSTRUMENT WITH FLEXIBLE ANTENNA ASSEMBLY AND METHOD

(75) Inventors: Jules Gauthier, Laval (CA); Dany Berube, Fremont, CA (US); Hiep Nguyen, Milpitas, CA (US)

(73) Assignee: AFx, Inc., Santa Clara, CA (US)

( * ) Notice: Subject to any disclaimer, the term of this patent is extended or adjusted under 35 U.S.C. 154(b) by 0 days.

(21) Appl. No.: 11/356,917

(22) Filed: Feb. 16, 2006

(65) Prior Publication Data

US 2006/0138122 A1    Jun. 29, 2006

Related U.S. Application Data

(60) Division of application No. 10/219,598, filed on Aug. 14, 2002, now abandoned, which is a continuation of application No. 09/484,548, filed on Jan. 18, 2000, now Pat. No. 7,033,352.

(51) Int. Cl.
*H05B 6/64* (2006.01)
*A61N 1/00* (2006.01)

(52) U.S. Cl. .................................. 219/679; 607/101

(58) Field of Classification Search ............... 219/543, 219/538, 540, 542, 679; 338/307; 174/250; 607/101, 100, 102; *H05B 6/64; A61N 1/00*
See application file for complete search history.

(56) References Cited

U.S. PATENT DOCUMENTS 1,586,645 A    6/1926  Bierman 3,598,108 A    8/1971  Jamshidi et al.

(Continued)

FOREIGN PATENT DOCUMENTS

EP    0048402 B1    8/1985

(Continued)

OTHER PUBLICATIONS

Andriole et al., "Biopsy Needle Characteristics Assessed in the Laboratory," Radiology, vol. 148, No. 3, Sep. 1983, pp. 659-662.

(Continued)

*Primary Examiner*—Daniel Robinson
(74) *Attorney, Agent, or Firm*—Fenwick & West LLP

(57) ABSTRACT

A flexible microwave antenna assembly for a surgical ablation instrument capable of conforming to a tissue surface for ablation thereof. The ablation instrument includes a transmission line having a proximal portion suitable for connection to an electromagnetic energy source. The antenna assembly includes a flexible antenna coupled to the transmission line for radially generating an electric field sufficiently strong to cause tissue ablation. A flexible shield device is coupled to the antenna to substantially shield a surrounding area of the antenna from the electric field radially generated therefrom while permitting a majority of the field to be directed generally in a predetermined direction. A flexible insulator is disposed between the shield device and the antenna which defines a window portion enabling the transmission of the directed electric field in the predetermined direction. The antenna, the shield device and the insulator are formed for selective manipulative bending thereof, as a unit, to one of a plurality of contact positions to generally conform the window portion to the biological tissue surface to be ablated.

3 Claims, 9 Drawing Sheets

U.S. PATENT DOCUMENTS

| | | |
|---|---|---|
| 3,827,436 A | 8/1974 | Stumpf et al. |
| 3,831,607 A | 8/1974 | Lindemann |
| 3,886,944 A | 6/1975 | Jamshidi |
| 3,976,082 A | 8/1976 | Schmitt |
| 4,011,872 A | 3/1977 | Komiya |
| 4,033,357 A | 7/1977 | Helland et al. |
| 4,045,056 A | 8/1977 | Kandakov et al. |
| 4,073,287 A | 2/1978 | Bradley et al. |
| 4,204,549 A | 5/1980 | Paglione |
| 4,244,371 A | 1/1981 | Farin |
| 4,268,937 A | 5/1981 | Grimshaw |
| 4,312,364 A | 1/1982 | Convert et al. |
| 4,409,993 A | 10/1983 | Furihata |
| 4,416,276 A | 11/1983 | Newton et al. |
| 4,445,892 A | 5/1984 | Hussein et al. |
| 4,448,198 A | 5/1984 | Turner |
| 4,462,412 A | 7/1984 | Turner |
| 4,465,079 A | 8/1984 | Dickhudt |
| 4,476,872 A | 10/1984 | Perlin |
| 4,494,539 A | 1/1985 | Zenitani et al. |
| 4,522,212 A | 6/1985 | Gelinas et al. |
| 4,564,200 A | 1/1986 | Loring et al. |
| 4,565,200 A | 1/1986 | Cosman |
| 4,573,473 A | 3/1986 | Hess |
| 4,583,556 A | 4/1986 | Hines et al. |
| 4,640,983 A | 2/1987 | Comte |
| 4,641,646 A | 2/1987 | Schultz et al. |
| 4,643,186 A | 2/1987 | Rosen et al. |
| 4,655,219 A | 4/1987 | Petruzzi |
| 4,657,015 A | 4/1987 | Irnich |
| 4,660,571 A | 4/1987 | Hess et al. |
| 4,681,122 A | 7/1987 | Winters et al. |
| 4,685,459 A | 8/1987 | Koch et al. |
| 4,699,147 A | 10/1987 | Chilson et al. |
| 4,700,716 A | 10/1987 | Kasevich et al. |
| 4,763,668 A | 8/1988 | Macek et al. |
| 4,785,815 A | 11/1988 | Cohen |
| 4,800,899 A | 1/1989 | Elliott |
| 4,823,812 A | 4/1989 | Eshel et al. |
| 4,825,880 A | 5/1989 | Stauffer et al. |
| 4,832,048 A | 5/1989 | Cohen |
| 4,841,988 A | 6/1989 | Fetter et al. |
| 4,841,990 A | 6/1989 | Kikuchi et al. |
| 4,881,543 A | 11/1989 | Trembly et al. |
| 4,891,483 A | 1/1990 | Kikuchi et al. |
| 4,920,978 A | 5/1990 | Colvin |
| 4,924,863 A | 5/1990 | Sterzer |
| 4,924,864 A | 5/1990 | Danzig |
| 4,932,420 A | 6/1990 | Goldstein |
| 4,938,217 A | 7/1990 | Lele |
| 4,945,912 A | 8/1990 | Langberg |
| 4,960,134 A | 10/1990 | Webster, Jr. |
| 4,966,597 A | 10/1990 | Cosman |
| 4,976,711 A | 12/1990 | Parins et al. |
| 5,007,437 A | 4/1991 | Sterzer |
| RE33,590 E | 5/1991 | Dory |
| 5,019,076 A | 5/1991 | Yamanashi et al. |
| 5,044,375 A | 9/1991 | Bach, Jr. et al. |
| 5,057,106 A | 10/1991 | Kasevich et al. |
| 5,078,713 A | 1/1992 | Varney |
| 5,080,101 A | 1/1992 | Dory |
| 5,080,102 A | 1/1992 | Dory |
| 5,085,659 A | 2/1992 | Rydell |
| 5,097,845 A | 3/1992 | Fetter et al. |
| 5,100,388 A | 3/1992 | Behl et al. |
| 5,104,393 A | 4/1992 | Isner et al. |
| 5,108,390 A | 4/1992 | Potocky et al. |
| 5,111,822 A | 5/1992 | Dory |
| 5,114,403 A | 5/1992 | Clarke et al. |
| 5,129,396 A | 7/1992 | Rosen et al. |
| 5,139,496 A | 8/1992 | Hed |
| 5,147,355 A | 9/1992 | Friedman et al. |
| 5,147,357 A | 9/1992 | Rose et al. |
| 5,150,717 A | 9/1992 | Rosen et al. |
| 5,156,151 A | 10/1992 | Imran |
| 5,158,092 A | 10/1992 | Glace |
| 5,171,255 A | 12/1992 | Rydell |
| 5,172,699 A | 12/1992 | Svenson et al. |
| 5,188,122 A | 2/1993 | Phipps et al. |
| 5,190,054 A | 3/1993 | Fetter et al. |
| 5,192,278 A | 3/1993 | Hayes et al. |
| 5,207,672 A | 5/1993 | Roth et al. |
| 5,207,674 A | 5/1993 | Hamilton |
| 5,222,501 A | 6/1993 | Ideker et al. |
| 5,230,334 A | 7/1993 | Klopotek |
| 5,230,349 A | 7/1993 | Langberg |
| 5,242,441 A | 9/1993 | Avitall |
| 5,246,438 A | 9/1993 | Langberg |
| 5,248,312 A | 9/1993 | Langberg |
| 5,263,493 A | 11/1993 | Avitall |
| 5,281,213 A | 1/1994 | Milder et al. |
| 5,281,215 A | 1/1994 | Milder |
| 5,281,217 A | 1/1994 | Edwards et al. |
| 5,293,869 A | 3/1994 | Edwards et al. |
| 5,295,484 A | 3/1994 | Marcus et al. |
| 5,295,955 A | 3/1994 | Rosen et al. |
| 5,300,068 A | 4/1994 | Rosar et al. |
| 5,300,099 A | 4/1994 | Rudie |
| 5,301,687 A | 4/1994 | Wong et al. |
| 5,304,207 A | 4/1994 | Stromer |
| 5,313,943 A | 5/1994 | Houser et al. |
| 5,314,466 A | 5/1994 | Stern et al. |
| 5,318,525 A | 6/1994 | West et al. |
| 5,323,781 A | 6/1994 | Ideker et al. |
| 5,327,889 A | 7/1994 | Imran |
| 5,334,168 A | 8/1994 | Hemmer |
| 5,341,807 A | 8/1994 | Nardella |
| 5,344,431 A | 9/1994 | Merritt et al. |
| 5,344,441 A | 9/1994 | Gronauer |
| 5,348,554 A | 9/1994 | Imran et al. |
| 5,358,515 A | 10/1994 | Hurter et al. |
| 5,364,336 A | 11/1994 | Carr |
| 5,364,351 A | 11/1994 | Heinzelman et al. |
| 5,364,352 A | 11/1994 | Cimino et al. |
| 5,364,392 A | 11/1994 | Warner et al. |
| 5,366,490 A | 11/1994 | Edwards et al. |
| 5,368,592 A | 11/1994 | Stern et al. |
| 5,369,251 A | 11/1994 | King et al. |
| 5,370,644 A | 12/1994 | Langberg |
| 5,370,675 A | 12/1994 | Edwards et al. |
| 5,370,677 A | 12/1994 | Rudie et al. |
| 5,370,678 A | 12/1994 | Edwards et al. |
| 5,374,287 A | 12/1994 | Rubin |
| 5,376,094 A | 12/1994 | Kline |
| 5,383,876 A | 1/1995 | Nardella |
| 5,383,922 A | 1/1995 | Zipes et al. |
| 5,391,147 A | 2/1995 | Imran et al. |
| 5,397,304 A | 3/1995 | Truckai |
| 5,398,683 A | 3/1995 | Edwards et al. |
| 5,402,772 A | 4/1995 | Moll et al. |
| 5,403,312 A | 4/1995 | Yates et al. |
| 5,405,346 A | 4/1995 | Grundy et al. |
| 5,405,375 A | 4/1995 | Ayers et al. |
| 5,405,376 A | 4/1995 | Mulier et al. |
| 5,415,656 A | 5/1995 | Tihon et al. |
| 5,417,208 A | 5/1995 | Winkler |
| 5,423,807 A | 6/1995 | Milder |
| 5,431,649 A | 7/1995 | Mulier et al. |
| 5,437,665 A | 8/1995 | Munro |
| 5,439,006 A | 8/1995 | Brennen et al. |
| 5,443,489 A | 8/1995 | Ben-Haim |
| 5,445,193 A | 8/1995 | Koeninger et al. |
| 5,450,846 A | 9/1995 | Goldreyer |
| 5,452,733 A | 9/1995 | Sterman et al. |

| | | | | | |
|---|---|---|---|---|---|
| 5,454,370 A | 10/1995 | Avitall | 5,735,280 A | 4/1998 | Sherman et al. |
| 5,454,733 A | 10/1995 | Watanabe et al. | 5,737,384 A | 4/1998 | Fenn |
| 5,454,807 A | 10/1995 | Lennox et al. | 5,738,096 A | 4/1998 | Ben-Haim |
| 5,462,544 A | 10/1995 | Saksena et al. | 5,741,225 A | 4/1998 | Lax et al. |
| 5,462,545 A | 10/1995 | Wang et al. | 5,741,249 A | 4/1998 | Moss et al. |
| 5,464,404 A | 11/1995 | Abela et al. | 5,743,239 A | 4/1998 | Iwase |
| 5,470,308 A | 11/1995 | Edwards et al. | 5,755,760 A | 5/1998 | Maguire et al. |
| 5,482,037 A | 1/1996 | Borghi | 5,762,066 A | 6/1998 | Law et al. |
| 5,484,433 A | 1/1996 | Taylor et al. | 5,762,626 A | 6/1998 | Lundquist et al. |
| 5,487,757 A | 1/1996 | Truckai et al. | 5,769,790 A | 6/1998 | Watkins et al. |
| 5,492,126 A | 2/1996 | Hennige et al. | 5,769,846 A | 6/1998 | Edwards et al. |
| 5,494,039 A | 2/1996 | Onik et al. | 5,782,747 A | 7/1998 | Zimmon |
| 5,496,271 A | 3/1996 | Burton et al. | 5,782,828 A | 7/1998 | Chen et al. |
| 5,496,312 A | 3/1996 | Klicek | 5,785,706 A | 7/1998 | Bednarek |
| 5,500,012 A | 3/1996 | Brucker et al. | 5,785,707 A | 7/1998 | Boyd et al. |
| 5,507,743 A | 4/1996 | Edwards et al. | 5,788,692 A | 8/1998 | Campbell et al. |
| 5,514,131 A | 5/1996 | Edwards et al. | 5,797,905 A | 8/1998 | Fleischman et al. |
| 5,520,188 A | 5/1996 | Hennige et al. | 5,797,960 A | 8/1998 | Stevens et al. |
| 5,529,820 A | 6/1996 | Nomi et al. | 5,800,378 A | 9/1998 | Edwards et al. |
| 5,531,677 A | 7/1996 | Lundquist et al. | 5,800,379 A | 9/1998 | Edwards |
| 5,536,247 A | 7/1996 | Thornton | 5,800,413 A | 9/1998 | Swartz et al. |
| 5,540,681 A | 7/1996 | Strul et al. | 5,800,428 A | 9/1998 | Nelson et al. |
| 5,540,684 A | 7/1996 | Hassler, Jr. | 5,800,482 A | 9/1998 | Pomeranz et al. |
| 5,545,193 A | 8/1996 | Fleischman et al. | 5,800,494 A | 9/1998 | Campbell et al. |
| 5,545,200 A | 8/1996 | West et al. | 5,807,309 A | 9/1998 | Lundquist et al. |
| 5,549,638 A | 8/1996 | Burdette | 5,807,395 A | 9/1998 | Mulier et al. |
| 5,549,644 A | 8/1996 | Lundquist et al. | 5,810,803 A | 9/1998 | Moss et al. |
| 5,549,661 A | 8/1996 | Kordis et al. | 5,814,028 A | 9/1998 | Swartz et al. |
| 5,569,242 A | 10/1996 | Lax et al. | 5,823,197 A | 10/1998 | Edwards |
| 5,571,088 A | 11/1996 | Lennox et al. | 5,823,955 A | 10/1998 | Kuck et al. |
| 5,571,215 A | 11/1996 | Sterman et al. | 5,823,956 A | 10/1998 | Roth et al. |
| 5,575,766 A | 11/1996 | Swartz et al. | 5,823,962 A | 10/1998 | Schaetzle et al. |
| 5,575,810 A | 11/1996 | Swanson et al. | 5,826,576 A | 10/1998 | West |
| 5,578,030 A | 11/1996 | Levin | 5,827,216 A | 10/1998 | Igo et al. |
| 5,578,067 A | 11/1996 | Ekwall et al. | 5,829,447 A | 11/1998 | Stevens et al. |
| 5,581,905 A | 12/1996 | Huelsman et al. | 5,836,947 A | 11/1998 | Fleischman et al. |
| 5,584,830 A | 12/1996 | Ladd et al. | 5,836,990 A | 11/1998 | Li |
| 5,590,657 A | 1/1997 | Cain et al. | 5,840,027 A | 11/1998 | Swartz et al. |
| 5,593,404 A | 1/1997 | Costello et al. | 5,840,030 A | 11/1998 | Ferek-Petric et al. |
| 5,593,405 A | 1/1997 | Osypka | 5,842,037 A | 11/1998 | Haartsen |
| 5,599,295 A | 2/1997 | Rosen et al. | 5,843,026 A | 12/1998 | Edwards et al. |
| 5,599,346 A | 2/1997 | Baker et al. | 5,843,075 A | 12/1998 | Taylor |
| 5,603,697 A | 2/1997 | Grundy et al. | 5,843,171 A | 12/1998 | Campbell et al. |
| 5,606,974 A | 3/1997 | Castellano et al. | 5,846,238 A | 12/1998 | Jackson et al. |
| 5,607,389 A | 3/1997 | Edwards et al. | 5,852,860 A | 12/1998 | Lorraine et al. |
| 5,628,771 A | 5/1997 | Mizukawa et al. | 5,853,366 A | 12/1998 | Dowlatshahi |
| 5,630,837 A | 5/1997 | Crowley | 5,853,368 A | 12/1998 | Solomon et al. |
| 5,640,955 A | 6/1997 | Ockuly et al. | 5,855,614 A | 1/1999 | Stevens et al. |
| 5,643,255 A | 7/1997 | Organ | 5,860,920 A | 1/1999 | McGee et al. |
| 5,658,280 A | 8/1997 | Issa | 5,861,002 A | 1/1999 | Desai |
| 5,672,172 A | 9/1997 | Zupkas | 5,861,021 A | 1/1999 | Thome et al. |
| 5,672,174 A | 9/1997 | Gough et al. | 5,863,290 A | 1/1999 | Gough et al. |
| 5,673,695 A | 10/1997 | McGee et al. | 5,868,737 A | 2/1999 | Taylor et al. |
| 5,676,692 A | 10/1997 | Sanghvi et al. | 5,871,481 A | 2/1999 | Kannenberg et al. |
| 5,676,693 A | 10/1997 | LaFontaine | 5,871,525 A | 2/1999 | Edwards et al. |
| 5,681,308 A | 10/1997 | Edwards et al. | 5,873,828 A | 2/1999 | Fujio et al. |
| 5,683,382 A | 11/1997 | Lenihan et al. | 5,873,896 A | 2/1999 | Ideker |
| 5,683,384 A | 11/1997 | Gough et al. | 5,882,302 A | 3/1999 | Driscoll, Jr. et al. |
| 5,687,723 A | 11/1997 | Avitall | 5,885,278 A | 3/1999 | Fleischman |
| 5,688,267 A | 11/1997 | Panescu et al. | 5,891,134 A * | 4/1999 | Goble et al. .................. 606/27 |
| 5,693,078 A | 12/1997 | Desai et al. | 5,895,355 A | 4/1999 | Schaer |
| 5,693,082 A | 12/1997 | Warner et al. | 5,897,553 A | 4/1999 | Mulier et al. |
| 5,694,701 A | 12/1997 | Huelsman et al. | 5,897,554 A | 4/1999 | Chia et al. |
| 5,697,928 A | 12/1997 | Walcott et al. | 5,899,899 A | 5/1999 | Arless et al. |
| 5,707,369 A | 1/1998 | Vaitekunas et al. | 5,904,709 A | 5/1999 | Arndt et al. |
| 5,718,226 A | 2/1998 | Riza | 5,906,580 A | 5/1999 | Kline-Schoder et al. |
| 5,718,241 A | 2/1998 | Ben-Haim et al. | 5,910,129 A | 6/1999 | Koblish et al. |
| 5,720,718 A | 2/1998 | Rosen et al. | 5,916,213 A | 6/1999 | Haissaguerre et al. |
| 5,720,775 A | 2/1998 | Larnard | 5,919,188 A | 7/1999 | Shearon et al. |
| 5,725,523 A | 3/1998 | Mueller | 5,921,924 A | 7/1999 | Avitall |
| 5,730,127 A | 3/1998 | Avitall | 5,924,424 A | 7/1999 | Stevens et al. |
| 5,733,280 A | 3/1998 | Avitall | 5,931,810 A | 8/1999 | Grabek |
| 5,733,281 A | 3/1998 | Nardella | 5,938,600 A | 8/1999 | Van Vaals et al. |

| | | | | | | |
|---|---|---|---|---|---|---|
| 5,938,612 | A | 8/1999 | Kline-Schoder et al. | 6,241,728 B1 | 6/2001 | Gaiser et al. |
| 5,938,692 | A | 8/1999 | Rudie | 6,241,754 B1 * | 6/2001 | Swanson et al. .............. 607/99 |
| 5,954,662 | A | 9/1999 | Swanson et al. | 6,245,062 B1 | 6/2001 | Berube et al. |
| 5,954,665 | A | 9/1999 | Ben-Haim | 6,245,064 B1 * | 6/2001 | Lesh et al. ..................... 606/34 |
| 5,957,842 | A | 9/1999 | Littmann et al. | 6,251,128 B1 | 6/2001 | Knopp et al. |
| 5,957,969 | A | 9/1999 | Warner et al. | 6,273,887 B1 | 8/2001 | Yamauchi et al. |
| 5,964,727 | A | 10/1999 | Edwards et al. | 6,277,113 B1 | 8/2001 | Berube |
| 5,964,732 | A | 10/1999 | Willard | 6,283,955 B1 | 9/2001 | Pacala et al. |
| 5,964,756 | A | 10/1999 | McGaffigan et al. | 6,287,302 B1 | 9/2001 | Berube |
| 5,971,983 | A | 10/1999 | Lesh | 6,289,249 B1 | 9/2001 | Arndt et al. |
| 5,978,714 | A | 11/1999 | Zadini et al. | 6,290,699 B1 | 9/2001 | Hall et al. |
| 5,980,697 | A | 11/1999 | Kolb et al. | 6,302,880 B1 | 10/2001 | Schaer |
| 5,993,389 | A | 11/1999 | Driscoll, Jr. et al. | 6,305,378 B1 * | 10/2001 | Lesh ........................... 128/898 |
| 5,993,445 | A | 11/1999 | Issa | 6,306,124 B1 | 10/2001 | Jones et al. |
| 5,993,447 | A | 11/1999 | Blewett et al. | 6,306,132 B1 | 10/2001 | Moorman et al. |
| 5,995,875 | A | 11/1999 | Blewett et al. | 6,309,388 B1 | 10/2001 | Fowler |
| 6,002,955 | A | 12/1999 | Willems et al. | 6,311,692 B1 | 11/2001 | Vaska et al. |
| 6,004,269 | A * | 12/1999 | Crowley et al. ............ 600/439 | 6,312,425 B1 | 11/2001 | Simpson et al. |
| 6,007,499 | A | 12/1999 | Martin et al. | 6,312,427 B1 | 11/2001 | Berube et al. |
| 6,010,516 | A | 1/2000 | Hulka | 6,314,962 B1 | 11/2001 | Vaska et al. |
| 6,027,497 | A | 2/2000 | Daniel et al. | 6,314,963 B1 | 11/2001 | Vaska et al. |
| 6,027,501 | A | 2/2000 | Goble et al. | 6,315,741 B1 | 11/2001 | Martin et al. |
| 6,030,382 | A | 2/2000 | Fleischman et al. | 6,322,558 B1 | 11/2001 | Taylor et al. |
| 6,032,077 | A | 2/2000 | Pomeranz | 6,325,796 B1 | 12/2001 | Berube et al. |
| 6,056,735 | A | 5/2000 | Okada et al. | 6,325,797 B1 | 12/2001 | Stewart et al. |
| 6,059,778 | A | 5/2000 | Sherman | 6,332,881 B1 | 12/2001 | Carner et al. |
| 6,063,077 | A | 5/2000 | Schaer | 6,346,104 B2 | 2/2002 | Daly et al. |
| 6,063,081 | A | 5/2000 | Mulier et al. | 6,355,033 B1 | 3/2002 | Moorman et al. |
| 6,064,902 | A | 5/2000 | Haissaguerre et al. | 6,356,790 B1 | 3/2002 | Maguire et al. |
| 6,066,094 | A | 5/2000 | Ben-Haim | 6,358,248 B1 | 3/2002 | Mulier et al. |
| 6,068,628 | A | 5/2000 | Fanton et al. | 6,361,531 B1 | 3/2002 | Hissong |
| 6,068,629 | A | 5/2000 | Haissaguerre et al. | 6,364,876 B1 | 4/2002 | Erb et al. |
| 6,071,274 | A | 6/2000 | Thompson et al. | 6,379,348 B1 | 4/2002 | Onik |
| 6,071,281 | A | 6/2000 | Burnside et al. | 6,383,182 B1 | 5/2002 | Berube et al. |
| 6,076,012 | A | 6/2000 | Swanson et al. | 6,402,556 B1 | 6/2002 | Lang et al. |
| 6,083,159 | A | 7/2000 | Driscoll, Jr. et al. | 6,413,254 B1 | 7/2002 | Hissong et al. |
| 6,086,583 | A | 7/2000 | Ouchi | 6,423,057 B1 | 7/2002 | He et al. |
| 6,090,104 | A | 7/2000 | Webster, Jr. | 6,423,059 B1 | 7/2002 | Hanson et al. |
| 6,090,105 | A | 7/2000 | Zepeda et al. | 6,428,538 B1 | 8/2002 | Blewett et al. |
| 6,097,985 | A | 8/2000 | Kasevich et al. | 6,430,426 B2 | 8/2002 | Avitall |
| 6,102,886 | A | 8/2000 | Lundquist et al. | 6,432,067 B1 | 8/2002 | Martin et al. |
| 6,106,517 | A | 8/2000 | Zupkas | 6,471,696 B1 | 10/2002 | Berube et al. |
| 6,106,521 | A | 8/2000 | Blewett et al. | 6,471,697 B1 | 10/2002 | Lesh |
| 6,106,522 | A | 8/2000 | Fleischman et al. | 6,474,340 B1 | 11/2002 | Vaska et al. |
| 6,106,524 | A | 8/2000 | Eggers et al. | 6,484,727 B1 | 11/2002 | Vaska et al. |
| 6,117,101 | A | 9/2000 | Diederich et al. | 6,488,639 B1 | 12/2002 | Ribault et al. |
| 6,119,041 | A | 9/2000 | Pomeranz et al. | 6,488,679 B1 | 12/2002 | Swanson et al. |
| 6,135,971 | A | 10/2000 | Hutchinson et al. | 6,490,474 B1 | 12/2002 | Willis et al. |
| 6,142,994 | A | 11/2000 | Swanson et al. | 6,500,133 B2 | 12/2002 | Martin et al. |
| 6,146,378 | A | 11/2000 | Mukus et al. | 6,502,575 B1 | 1/2003 | Jacobs et al. |
| 6,146,379 | A | 11/2000 | Fleischman et al. | 6,502,576 B1 * | 1/2003 | Lesh ........................... 128/898 |
| 6,152,920 | A | 11/2000 | Thompson et al. | 6,508,774 B1 | 1/2003 | Acker et al. |
| 6,161,543 | A | 12/2000 | Cox et al. | 6,514,246 B1 | 2/2003 | Swanson et al. |
| 6,162,216 | A | 12/2000 | Guziak et al. | 6,514,249 B1 | 2/2003 | Maguire et al. |
| 6,164,283 | A | 12/2000 | Lesh | 6,517,568 B1 | 2/2003 | Sharkey et al. |
| 6,165,174 | A | 12/2000 | Jacobs et al. | 6,526,320 B2 | 2/2003 | Mitchell |
| 6,171,303 | B1 | 1/2001 | Ben-Haim et al. | 6,527,767 B2 | 3/2003 | Wang et al. |
| 6,174,309 | B1 | 1/2001 | Wrublewski et al. | 6,527,768 B2 | 3/2003 | Berube |
| 6,178,354 | B1 | 1/2001 | Gibson | 6,529,756 B1 | 3/2003 | Phan et al. |
| 6,182,664 | B1 | 2/2001 | Cosgrove | 6,533,780 B1 | 3/2003 | Laird et al. |
| 6,190,382 | B1 | 2/2001 | Ormsby et al. | 6,542,781 B1 | 4/2003 | Koblish et al. |
| 6,200,315 | B1 | 3/2001 | Gaiser et al. | 6,576,875 B1 | 6/2003 | Kleffner et al. |
| 6,206,831 | B1 | 3/2001 | Suorsa et al. | 6,586,040 B1 | 7/2003 | Von Falkenhausen |
| 6,210,356 | B1 | 4/2001 | Anderson et al. | 6,599,280 B1 * | 7/2003 | Pynson et al. .............. 604/403 |
| 6,216,027 | B1 | 4/2001 | Willis et al. | 6,610,055 B1 | 8/2003 | Swanson et al. |
| 6,217,530 | B1 | 4/2001 | Martin et al. | 6,645,200 B1 | 11/2003 | Koblish et al. |
| 6,217,573 | B1 | 4/2001 | Webster | 6,645,202 B1 | 11/2003 | Pless et al. |
| 6,224,587 | B1 | 5/2001 | Gibson | 6,652,513 B2 | 11/2003 | Panescu et al. |
| 6,231,518 | B1 | 5/2001 | Grabek et al. | 6,652,515 B1 * | 11/2003 | Maguire et al. .............. 606/41 |
| 6,233,490 | B1 | 5/2001 | Kasevich | 6,652,518 B2 | 11/2003 | Wellman et al. |
| 6,235,025 | B1 | 5/2001 | Swartz et al. | 6,663,622 B1 | 12/2003 | Foley et al. |
| 6,237,605 | B1 | 5/2001 | Vaska et al. | 6,673,068 B1 | 1/2004 | Berube |
| 6,241,722 | B1 | 6/2001 | Dobak et al. | 6,689,062 B1 | 2/2004 | Mesallum |

| | | |
|---|---|---|
| 6,689,128 B2 | 2/2004 | Sliwa, Jr. et al. |
| 6,701,931 B2 | 3/2004 | Sliwa, Jr. et al. |
| 6,719,755 B2 | 4/2004 | Sliwa, Jr. et al. |
| 6,723,092 B2 | 4/2004 | Brown et al. |
| 6,802,840 B2 | 10/2004 | Chin et al. |
| 6,805,709 B1 | 10/2004 | Schaldach et al. |
| 6,808,536 B2 | 10/2004 | Wright et al. |
| 2001/0031961 A1 | 10/2001 | Hooven |
| 2001/0039416 A1 | 11/2001 | Moorman et al. |
| 2002/0001655 A1 | 1/2002 | Kuechle et al. |
| 2002/0017306 A1 | 2/2002 | Cox et al. |
| 2002/0032440 A1 | 3/2002 | Hooven et al. |
| 2002/0042610 A1 | 4/2002 | Sliwa, Jr. et al. |
| 2002/0042611 A1 | 4/2002 | Silwa et al. |
| 2002/0045895 A1 | 4/2002 | Sliwa, Jr. et al. |
| 2002/0058932 A1 | 5/2002 | Moorman |
| 2002/0087151 A1 | 7/2002 | Mody et al. |
| 2002/0087157 A1 | 7/2002 | Sliwa, Jr. et al. |
| 2002/0091382 A1 | 7/2002 | Hooven |
| 2002/0091383 A1 | 7/2002 | Hooven |
| 2002/0091384 A1 | 7/2002 | Hooven et al. |
| 2002/0095145 A1 | 7/2002 | Simons et al. |
| 2002/0103484 A1 | 8/2002 | Hooven |
| 2002/0107513 A1 | 8/2002 | Hooven |
| 2002/0107514 A1 | 8/2002 | Hooven |
| 2002/0111613 A1 | 8/2002 | Berube |
| 2002/0115993 A1 | 8/2002 | Hooven |
| 2002/0120263 A1 | 8/2002 | Brown et al. |
| 2002/0120267 A1 | 8/2002 | Phan |
| 2002/0120316 A1 | 8/2002 | Hooven et al. |
| 2002/0128639 A1 | 9/2002 | Pless et al. |
| 2002/0128642 A1 | 9/2002 | Berube et al. |
| 2002/0173784 A1 | 11/2002 | Sliwa, Jr. et al. |
| 2002/0193783 A1 | 12/2002 | Gauthier et al. |
| 2002/0193786 A1 | 12/2002 | Berube et al. |
| 2003/0024537 A1 | 2/2003 | Cox et al. |
| 2003/0028187 A1 | 2/2003 | Vaska et al. |
| 2003/0029462 A1 | 2/2003 | Cox et al. |
| 2003/0032952 A1 | 2/2003 | Hooven |
| 2003/0050630 A1 | 3/2003 | Mody et al. |
| 2003/0050631 A1 | 3/2003 | Mody et al. |
| 2003/0065327 A1 | 4/2003 | Wellman et al. |
| 2003/0069572 A1 | 4/2003 | Wellman et al. |
| 2003/0069574 A1 | 4/2003 | Sliwa, Jr. et al. |
| 2003/0069575 A1 | 4/2003 | Fatt et al. |
| 2003/0069577 A1 | 4/2003 | Vaska et al. |
| 2003/0073988 A1 | 4/2003 | Berube et al. |
| 2003/0073992 A1 | 4/2003 | Sliwa, Jr. et al. |
| 2003/0078571 A1 | 4/2003 | Sliwa, Jr. et al. |
| 2003/0079753 A1 | 5/2003 | Vaska et al. |
| 2003/0083654 A1 | 5/2003 | Fatt et al. |
| 2003/0093068 A1 | 5/2003 | Hooven |
| 2003/0097126 A1 | 5/2003 | Woloszko et al. |
| 2003/0109868 A1 | 6/2003 | Fatt et al. |
| 2003/0125666 A1 | 7/2003 | Kashara et al. |
| 2003/0125725 A1 | 7/2003 | Woodard et al. |
| 2003/0125729 A1 | 7/2003 | Hooven et al. |
| 2003/0136951 A1 | 7/2003 | Hung |
| 2003/0158547 A1 | 8/2003 | Phan |
| 2003/0158548 A1 | 8/2003 | Phan et al. |
| 2003/0163128 A1 | 8/2003 | Patil et al. |
| 2003/0171745 A1 | 9/2003 | Francischelli et al. |
| 2003/0176764 A1 | 9/2003 | Fiegel et al. |
| 2003/0181907 A1 | 9/2003 | Lindsay |
| 2004/0002045 A1 | 1/2004 | Wellman et al. |
| 2004/0044340 A1 | 3/2004 | Francischelli et al. |
| 2004/0049179 A1 | 3/2004 | Francischelli et al. |
| 2004/0049208 A1 | 3/2004 | Hill et al. |
| 2004/0068274 A1 | 4/2004 | Hooven |
| 2004/0092990 A1 | 5/2004 | Opie et al. |
| 2004/0106918 A1 | 6/2004 | Cox et al. |

FOREIGN PATENT DOCUMENTS

| | | |
|---|---|---|
| EP | 0358 336 A1 | 3/1990 |
| EP | 0139607 B1 | 4/1990 |
| EP | 0248758 B1 | 8/1991 |
| EP | 0628322 A2 | 12/1994 |
| EP | 0738501 B1 | 5/2000 |
| EP | 1005838 A1 | 6/2000 |
| EP | 1042990 A1 | 10/2000 |
| EP | 0655 225 B1 | 3/2001 |
| EP | 118310 A1 | 7/2001 |
| EP | 0839547 B2 | 9/2003 |
| WO | WO 93/08757 | 5/1993 |
| WO | WO 93/15664 | 8/1993 |
| WO | WO 93/20767 | 10/1993 |
| WO | WO 93/20768 | 10/1993 |
| WO | WO 93/20886 | 10/1993 |
| WO | WO 93/20893 | 10/1993 |
| WO | WO 93/24065 | 12/1993 |
| WO | WO 93/02204 | 2/1994 |
| WO | WO 95/05212 | 2/1995 |
| WO | WO 95/18575 | 7/1995 |
| WO | WO 96/26675 | 9/1996 |
| WO | WO 95/35469 A1 | 11/1996 |
| WO | WO 96/35496 | 11/1996 |
| WO | WO 96/36397 | 11/1996 |
| WO | WO 97/42893 | 11/1997 |
| WO | WO 97/44092 A | 11/1997 |
| WO | WO 98/06341 | 2/1998 |
| WO | WO 98/17185 | 4/1998 |
| WO | WO 98/17187 | 4/1998 |
| WO | WO 98/44857 | 10/1998 |
| WO | WO 99/04696 | 2/1999 |
| WO | WO 99/08613 | 2/1999 |
| WO | WO 99/34860 | 7/1999 |
| WO | WO 99/59486 | 11/1999 |
| WO | WO 00/16850 | 3/2000 |
| WO | WO 00/35363 | 6/2000 |
| WO | WO 00/56239 | 9/2000 |
| WO | WO 01/05306 | 1/2001 |
| WO | WO 01/15616 A1 | 3/2001 |
| WO | WO 01/41664 A | 6/2001 |
| WO | WO 01/58373 A1 | 8/2001 |
| WO | WO 01/80755 A2 | 11/2001 |
| WO | WO 01/82814 A2 | 11/2001 |
| WO | WO 02/01655 A2 | 1/2002 |
| WO | WO 02/05722 A1 | 1/2002 |
| WO | WO 02/38052 A2 | 5/2002 |
| WO | WO 02/060523 A2 | 8/2002 |

OTHER PUBLICATIONS

Arendt-Nielsen et al., "Selectivity of Spatial Filters for Surface EMG Detection from the Tibialis Anterior Muscle," [online], © [retrieved Nov. 23, 2003], 2 pages, Retrieved from the Internet <URL:http://www.lisin.polito.it/english/annual_reports/ar2002_uk/19uk.htm.

Cheng, "Field and Wave Electromagnetics," 1989, Addison Wesley Publishing Co., Inc., pp. 485-509.

Cox, J.L., "The Surgical Treatment of Atrial Fibrillation," J Thorac Cardiovasc Surg, 1991, pp. 584-592, vol. 101.

Gauthier, et al., "A Microwave Ablation Instrument with Flexible Antenna Assembly and Method," U.S. Appl. No. 09/484,548, filed Jan. 18, 2000.

Gottlieb et al., "Interstial Microwave Hyperthermia Applicators Having Submillimetre Diameters," Int. J. Hyperthermia, vol. 6, No. 3, 1990, pp. 707-714.

Haines et al., "Tissue Heating During Radiofrequency Catheter Ablation: A Thermodynamic Model and Observation in Isolated Perfused and Superfused Canine Right Ventricular Free Wall," Pacint Clin Electrophysol, Jun. 1989, 12(6), pp. 962-976.

Knaut et al., "Intraoperative Microwave Ablation for Curative Treatment of Atrial Fibrillation in Open Heart Surgery, The MICRO-STAF and MICRO-PASS Pilot Trial,"Thorac Cardiovasc. Surg. 47, (Supp.), 1999, pp. 379-384.

Labonte et al., "Monopole Antennas for Microwave Catheter Ablation," IEEE Transactions on Microwave Theory and Techniques, vol. 44, No. 10, Oct. 1996, pp. 1832-1840.

Langberg et al., "Catheter Ablation of the Atrioventricular Junction Using a Helical Microwave Antenna: A Novel Means of Coupling Energy to Endocardium," Pace, vol. 14, Dec. 1991, pp. 2105-2113.

Liem et al., Microwave Linear Ablation of the Isthmus Between the Inferior Vena Cava and Tricuspid Annulus, Pacing and Clinical Electrophysiology, Nov. 1998, pp. 2079-2085, vol. 21, No. 11, Pt. 1.

Matsukawa et al., "Percutaneous Microwave Coagulation Therapy In Liver Tumors: A 3-Year Experience," Acta Radiologica, vol. 38, 1997, pp. 410-415.

Murakami et al., "Treatment of Hepatocellular Carcinoma: Value of Percutaneous Microwave Coagulation," American Journal of Roentgenology, vol. 164, No. 5, May 1995, pp. 1159-1164.

Sato et al., "Microwave Coagulation Therapy for Hepatocellular Carcinoma," Gastroenterology, vol. 110, No. 5, May 1996, pp. 1507-1514.

Sato et al., "Two Long-Term Survivors AFter Microwave Coagulation Therapy for Heptocellular Carcinoma: A Case Report,", Hepatogastroenterology, vol. 43, No. 10, Jul. 1996, pp. 1035-1039.

Seki et al., "Ultrasonically Guided Percutaneous Microwave Coagulation Therapy for Small Hepatocellular Carcinoma," Cancer, vol. 74, No. 3, Aug. 1, 1994, pp. 817-825.

* cited by examiner

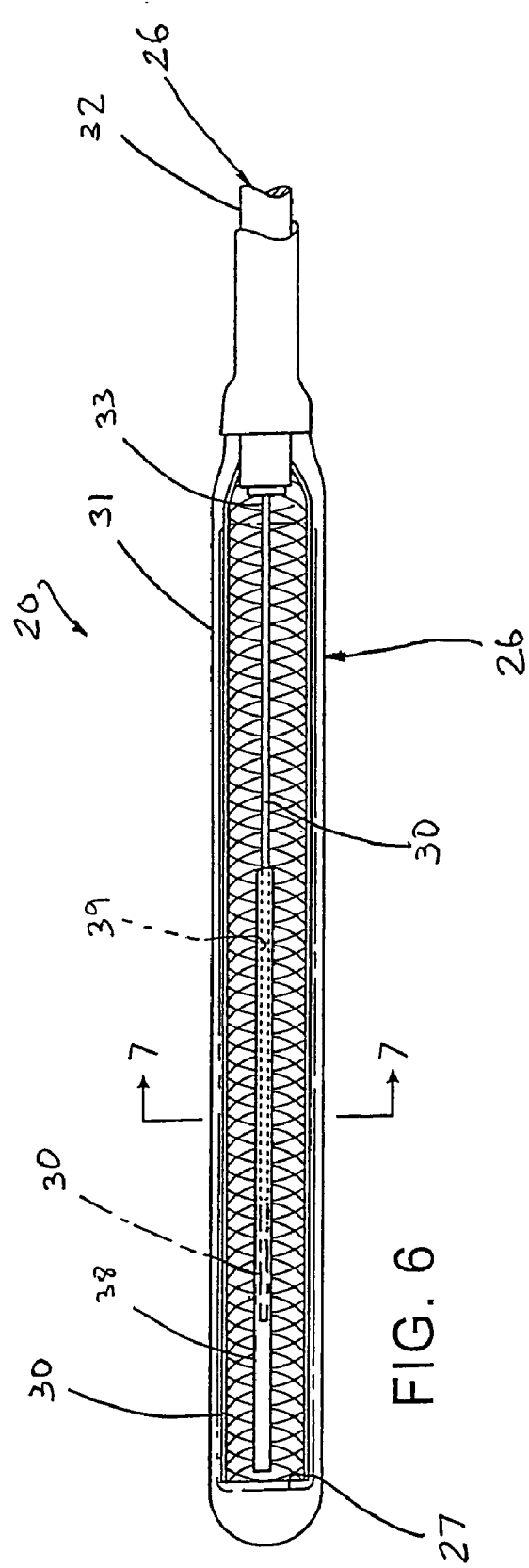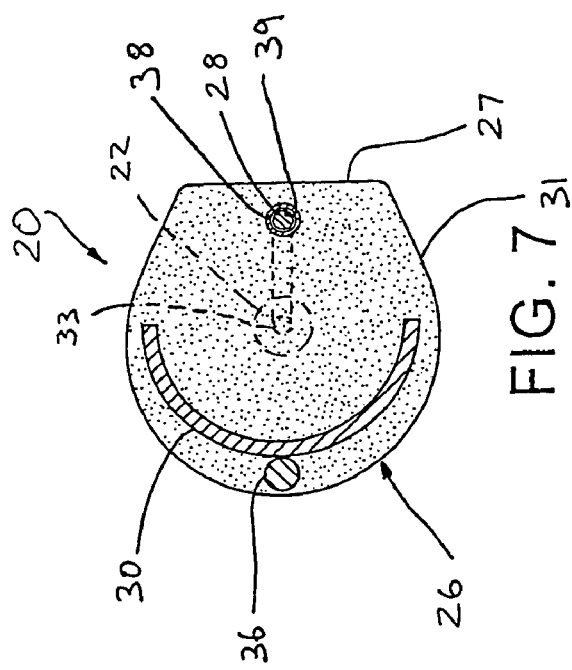

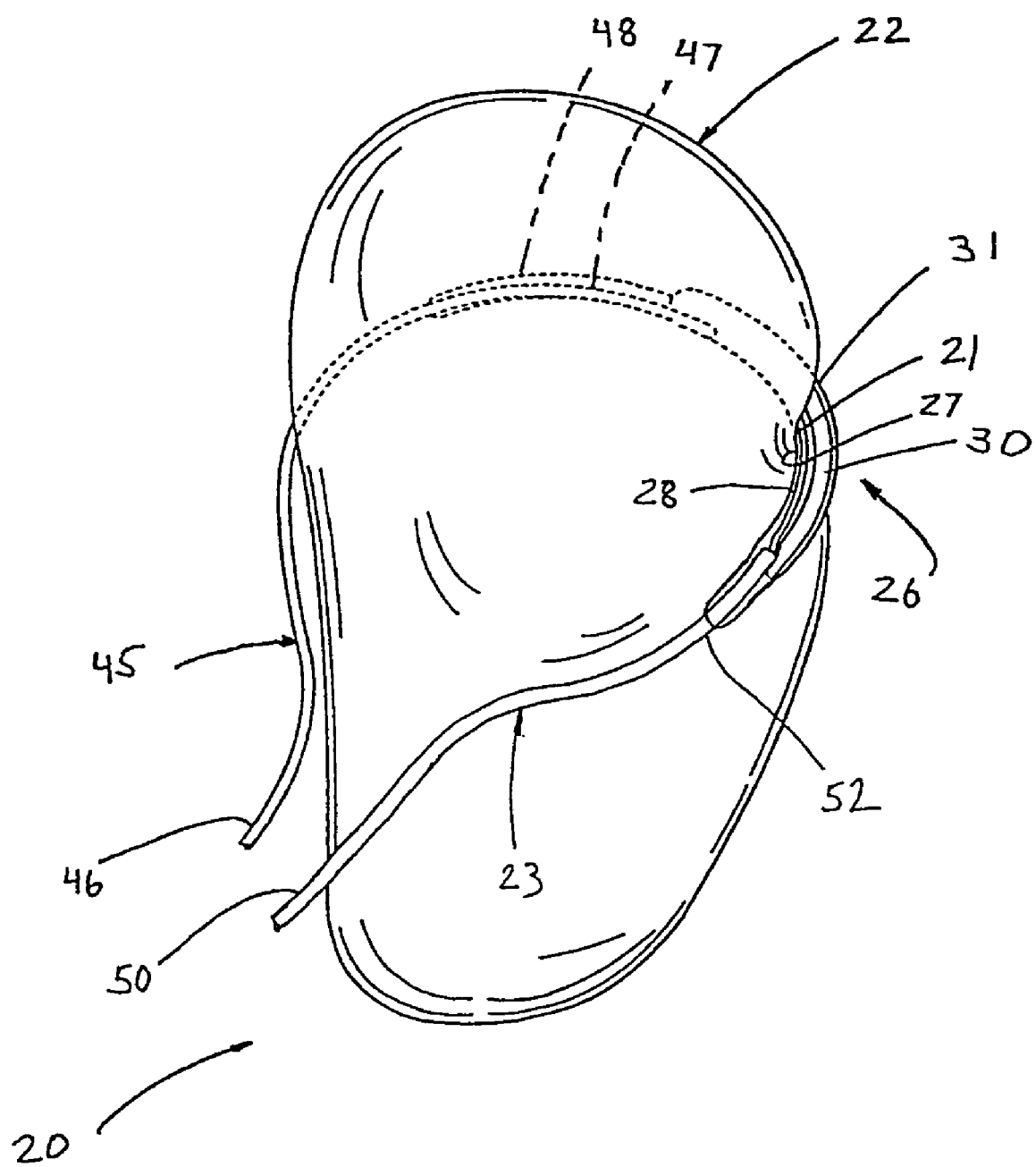
FIG._12

MICROWAVE ABLATION INSTRUMENT WITH FLEXIBLE ANTENNA ASSEMBLY AND METHOD

RELATED APPLICATIONS

This application claims the benefit under 35 U.S.C. §120 as a division of application Ser. No. 10/219,598 filed on Aug. 14, 2002, which is a continuation of application Ser. No. 09/484,548, filed Jan. 18, 2000, now U.S. Pat. No. 7,033,352 entitled "A MICROWAVE ABLATION INSTRUMENT WITH FLEXIBLE ANTENNA ASSEMBLY AND METHOD," which applications are incorporated herein in the entirety by this reference thereto.

BACKGROUND OF THE INVENTION

1. Field of Invention

The present invention relates, generally, to ablation instrument systems that use electromagnetic energy in the microwave frequencies to ablate internal bodily tissues, and, more particularly, to antenna arrangements and instrument construction techniques that direct the microwave energy in selected directions that are relatively closely contained along the antenna.

2. Description of the Prior Art

It is well documented that atrial fibrillation, either alone or as a consequence of other cardiac disease, continues to persist as the most common cardiac arrhythmia. According to recent estimates, more than two million people in the U.S. suffer from this common arrhythmia, roughly 0.15% to 2.0% of the population. Moreover, the prevalence of this cardiac disease increases with age, affecting nearly 8% to 17% of those over 60 years of age.

Atrial arrhythmia may be treated using several methods. Pharmacological treatment of atrial fibrillation, for example, is initially the preferred approach, first to maintain normal sinus rhythm, or secondly to decrease the ventricular response rate. Other forms of treatment include chemical cardioversion to normal sinus rhythm, electrical cardioversion, and RF catheter ablation of selected areas determined by mapping. In the more recent past, other surgical procedures have been developed for atrial fibrillation, including left atrial isolation, transvenous catheter or cryosurgical ablation of His bundle, and the Corridor procedure, which have effectively eliminated irregular ventricular rhythm. However, these procedures have for the most part failed to restore normal cardiac hemodynamics, or alleviate the patient's vulnerability to thromboembolism because the atria are allowed to continue to fibrillate. Accordingly, a more effective surgical treatment was required to cure medically refractory atrial fibrillation of the heart.

On the basis of electrophysiologic mapping of the atria and identification of macroreentrant circuits, a surgical approach was developed which effectively creates an electrical maze in the atrium (i.e., the MAZE procedure) and precludes the ability of the atria to fibrillate. Briefly, in the procedure commonly referred to as the MAZE III procedure, strategic atrial incisions are performed to prevent atrial reentry and allow sinus impulses to activate the entire atrial myocardium, thereby preserving atrial transport function postoperatively. Since atrial fibrillation is characterized by the presence of multiple macroreentrant circuits that are fleeting in nature and can occur anywhere in the atria, it is prudent to interrupt all of the potential pathways for atrial macroreentrant circuits. These circuits, incidentally, have been identified by intraoperative mapping both experimentally and clinically in patients.

Generally, this procedure includes the excision of both atrial appendages, and the electrical isolation of the pulmonary veins. Further, strategically placed atrial incisions not only interrupt the conduction routes of the common reentrant circuits, but they also direct the sinus impulse from the sinoatrial node to the atrioventricular node along a specified route. In essence, the entire atrial myocardium, with the exception of the atrial appendages and the pulmonary veins, is electrically activated by providing for multiple blind alleys off the main conduction route between the sinoatrial node to the atrioventricular node. Atrial transport function is thus preserved postoperatively as generally set forth in the series of articles: Cox, Schuessler, Boineau, Canavan, Cain, Lindsay, Stone, Smith, Corr, Change, and D'Agostino, Jr., *The Surgical Treatment Atrial Fibrillation* (pts. 1-4), 101 THORAC CARDIOVASC SURG., 402-426, 569-592 (1991).

While this MAZE III procedure has proven effective in ablating medically refractory atrial fibrillation and associated detrimental sequelae, this operational procedure is traumatic to the patient since substantial incisions are introduced into the interior chambers of the heart. Consequently, other techniques have thus been developed to interrupt and redirect the conduction routes without requiring substantial atrial incisions. One such technique is strategic ablation of the atrial tissues through ablation catheters.

Most approved ablation catheter systems now utilize radio frequency (RF) energy as the ablating energy source. Accordingly, a variety of RF based catheters and power supplies are currently available to electrophysiologists. However, radio frequency energy has several limitations including the rapid dissipation of energy in surface tissues resulting in shallow "burns" and failure to access deeper arrhythmic tissues. Another limitation of RF ablation catheters is the risk of clot formation on the energy emitting electrodes. Such clots have an associated danger of causing potentially lethal strokes in the event that a clot is dislodged from the catheter.

As such, catheters which utilize electromagnetic energy in the microwave frequency range as the ablation energy source are currently being developed. Microwave frequency energy has long been recognized as an effective energy source for heating biological tissues and has seen use in such hyperthermia applications as cancer treatment and preheating of blood prior to infusions. Accordingly, in view of the drawbacks of the traditional catheter ablation techniques, there has recently been a great deal of interest in using microwave energy as an ablation energy source. The advantage of microwave energy is that it is much easier to control and safer than direct current applications and it is capable of generating substantially larger lesions than RF catheters, which greatly simplifies the actual ablation procedures. Such microwave ablation systems are described in the U.S. Pat. No. 4,641,649 to Walinsky; U.S. Pat. No. 5,246,438 to Langberg; U.S. Pat. No. 5,405,346 to Grundy, et al.; and U.S. Pat. No. 5,314,466 to Stem, et al, each of which is incorporated herein by reference.

Most of the existing microwave ablation catheters contemplate the use of longitudinally extending helical antenna coils that direct the electromagnetic energy in a radial direction that is generally perpendicular to the longitudinal axis of the catheter although the fields created are not well constrained to the antenna itself. Although such catheter designs work well for a number of applications, such as radial output, they are inappropriate for use in precision surgical procedures. For example, in MAZE II surgical procedures, very precise and strategic lesions must be formed in the heart tissue which the existing microwave ablation catheters are incapable of delivering.

Consequently, microwave ablation instruments have recently been developed which incorporate microwave antennas having directional reflectors. Typically, a tapered directional reflector is positioned peripherally around the microwave antenna to direct the waves toward and out of a window portion of the antenna assembly. These ablation instruments, thus, are capable of effectively transmitting electromagnetic energy in a more specific direction. For example, the electromagnetic energy may be transmitted generally perpendicular to the longitudinal axis of the catheter but constrained to a selected angular section of the antenna, or directly out the distal end of the instrument. Typical of these designs are described in the U.S. patent application Ser. No. 09/178,066, filed Oct. 23, 1998; and Ser. No. 09/333,747, filed Jun. 14, 1999, each of which is incorporated herein by reference.

In these designs, the of the microwave antenna is preferably tuned assuming contact between the targeted tissue and a contact region of the antenna assembly extending longitudinally adjacent to the antenna longitudinal axis. Hence, should a portion of, or substantially all of, the exposed contact region of the antenna not be in contact with the targeted tissue during ablation, the adaptation of the antenna will be adversely changed and the antenna will be untuned. As a result, the portion of the antenna not in contact with the targeted tissue will radiate the electromagnetiz radiation into the surrounding air. The efficiency of the energy delivery into the tissue will consequently decrease which in turn causes the penetration depth of the lesion to decrease.

This is particularly problematic when the tissue surfaces are substantially curvilinear, or when the targeted tissue for ablation is difficult to access. Since these antenna designs are generally relatively rigid, it is often difficult to maneuver substantially all of the exposed contact region of the antenna into abutting contact against the targeted tissue. In these instances, several ablation instruments, having antennas of varying length and shape, may be necessary to complete just one series of ablations.

SUMMARY OF THE INVENTION

Accordingly, a flexible microwave antenna assembly is provided for a surgical ablation instrument adapted to ablate a surface of a biological tissue. The ablation instrument includes a transmission line having a proximal portion suitable for connection to an electromagnetic energy source. The antenna assembly includes a flexible antenna coupled to the transmission line for radially generating an electric field sufficiently strong to cause tissue ablation. A flexible shield device is coupled to the antenna to substantially shield a surrounding area of the antenna from the electric field radially generated therefrom while permitting a majority of the field to be directed generally in a predetermined direction. A flexible insulator is disposed between the shield device and the antenna which defines a window portion enabling the transmission of the directed electric field in the predetermined direction. In accordance with the present invention, the antenna, the shield device and the insulator are formed for selective manipulative bending thereof, as a unit, to one of a plurality of contact positions to generally conform the window portion to the biological tissue surface to be ablated.

In one configuration, a longitudinal axis of the antenna is off-set from a longitudinal axis of the insulator to position the antenna substantially proximate to and adjacent the window portion. The shield device is in the shape of a semi-cylindrical shell having a longitudinal axis generally co-axial with a longitudinal axis of the insulator.

In another embodiment, the insulator defines a receiving passage formed for sliding receipt of the antenna longitudinal therein during manipulative bending of the antenna assembly. Moreover, a polyimide tube device may be positioned in the receiving passage proximate the distal end of the antenna. The tube provides a bore formed and dimensioned sliding longitudinal reciprocation therein of at least the distal end of the antenna.

Another embodiment of the present invention provides an elongated, bendable, retaining member adapted for longitudinal coupling therealong to the insulator. This bendable retaining member enables the insulator to retain the one contact position after manipulative bending thereof for the conformance of the window portion to the biological tissue surface to be ablated. The retaining member is preferably disposed longitudinally along the insulator, and on one the of the shield device, while the antenna is preferably disposed on an opposite side of the shield device, longitudinally along the insulator, and between the shield device and the window portion.

In another aspect of the present invention provides a microwave ablation instrument, adapted to ablate a surface of a biological tissue, is provided having a handle member formed for manual manipulation of the ablation instrument. An elongated transmission line is provided coupled to the handle member. A proximal portion of the transmission line is suitable for connection to an electromagnetic energy source. The ablation instrument further includes a flexible antenna assembly coupled to the handle member which is formed for selective manipulative bending thereof. The antenna assembly includes a flexible antenna coupled to the transmission line for radially generating an electric field sufficiently strong to cause tissue ablation. A flexible shield device of the antenna assembly is employed to substantially shield a surrounding radial area of the antenna from the electric field radially generated therefrom, while permitting a majority of the field to be directed generally in a predetermined direction. A flexible insulator is disposed between the shield device and the antenna, and defines a window portion enabling the transmission of the directed electric field in the predetermined direction. The antenna, the shield device and the insulator are formed for selective manipulative bending thereof, as a unit, to one of a plurality of contact positions to generally conform the window portion to the biological tissue surface to be ablated.

In this configuration, the ablation instrument may include a bendable, malleable shaft having a proximal portion coupled to the handle member, and an opposite a distal portion coupled to the antenna assembly. The shaft is preferably a semi-rigid coaxial cable, but may also include a tubular shaft where the transmission line may be disposed therethrough from the proximal portion to the distal portion thereof. The shaft is preferably conductive having a distal portion conductively coupled to the proximal end of the shield device, and another portion conductively coupled to the outer conductor of the transmission line.

In another embodiment, a restraining sleeve is adapted to limit the bending movement of the bendable antenna assembly at the conductive coupling between the shield device and the shaft. The restraining sleeve is formed and dimensioned to extend peripherally over the conductive coupling to limit the bending movement in a predetermined direction to maintain the integrity of conductive coupling. The restraining sleeve includes a curvilinear transverse cross-sectional dimension extending past the conductive coupling longitudinally therealong by an amount sufficient to maintain the integrity.

In still another configuration, an elongated grip member is included having a distal grip portion and an opposite proximal portion coupled to a distal portion of the antenna assembly. The grip member and the handle member cooperate to selectively bend the antenna assembly and selectively urge the window portion in abutting contact with the biological tissue surface to be ablated. The gripping member is preferably provided by an elongated flexible rod having a diameter smaller than a diameter of the insulator. A longitudinal axis of the flexible rod is off-set from the longitudinal axis of the insulator to position the rod in general axial alignment with the antenna, and adjacent the window portion.

In still another aspect of the present invention, a method is provided for ablating medically refractory atrial fibrillation of the heart including the step of providing a microwave ablation instrument having a flexible antenna assembly adapted to generate an electric field sufficiently strong to cause tissue ablation. The antenna assembly defines a window portion enabling the transmission of the electric field there through in a predetermined direction. The method further includes selectively bending and retaining the flexible antenna assembly in one of a plurality of contact positions to generally conform the shape of the window portion to the targeted biological tissue surface to be ablated, and manipulating the ablation instrument to strategically position the conformed window portion into contact with the targeted biological tissue surface. The next step includes forming an elongated lesion in the targeted biological tissue surface through the generation of the electric field by the antenna assembly.

These bending, manipulating and generating events are preferably repeated to form a plurality of strategically positioned ablation lesions. Collectively, these lesions are formed to create a predetermined conduction pathway between a sinoatrial node and an atrioventricular node of the heart.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

FIG. 6 is a fragmentary side elevation view of the antenna assembly of FIG. 5.

FIG. 7 is an enlarged, front elevation view, in cross-section, of the antenna assembly taken substantially along the plane of the line 7-7 in FIG. 6.

FIG. 12 is a reduced, fragmentary, top perspective view of an alternative embodiment antenna assembly of FIG. 10 having a flexible handle member.

DETAILED DESCRIPTION OF THE INVENTION

Figure 1:
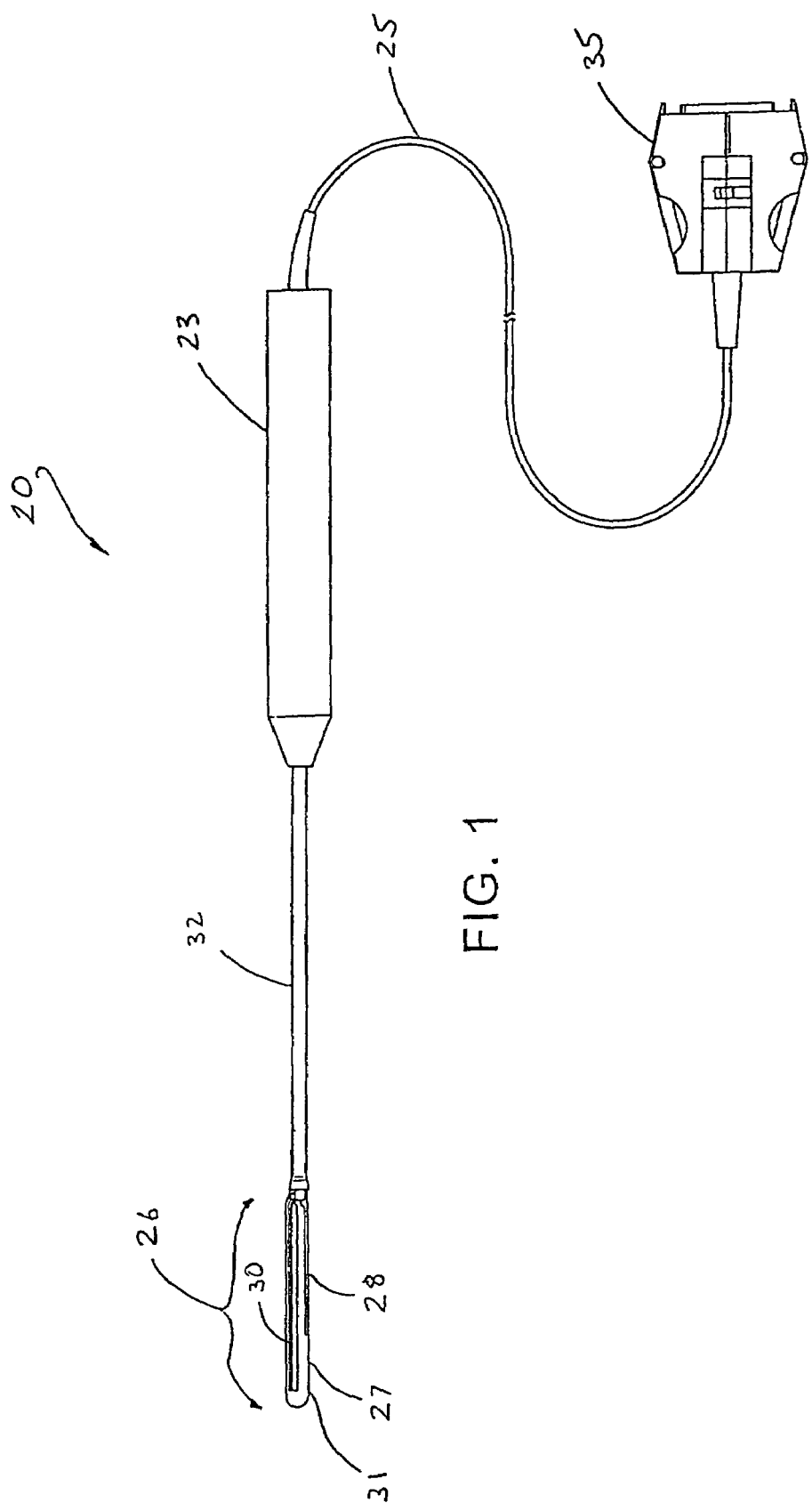
FIG. 1 is a diagrammatic top plan view of a microwave ablation instrument system with a bendable directional reflective antenna assembly constructed in accordance with one embodiment of the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various Figures.

Turning now to FIGS. 1-4, a microwave ablation instrument, generally designated 20, is provided which is adapted to ablate a surface 21 of a biological tissue 22. The ablation instrument 20 includes a handle member 23 formed to manually manipulate the instrument during open surgery. An elongated transmission line 25 is provided coupled to the handle member 23 at a distal portion thereof, and having a proximal portion suitable for connection to an electromagnetic energy source (not shown). The ablation instrument 20 further includes a flexible antenna assembly, generally designated 26, coupled to the handle member 23 and to the transmission line 25 to generate an electric field. The antenna assembly 26 is adapted to transmit an electric field out of a window portion 27 thereof in a predetermined direction sufficiently strong to cause tissue ablation. The antenna assembly is further formed for selective manipulative bending to one of a plurality of contact positions (e.g., FIGS. 3 and 4) to generally conform the window portion 27 to the biological tissue surface 21 to be ablated.

More specifically, the flexible antenna assembly 26 includes a flexible antenna 28 coupled to the transmission line 25 for radially generating the electric field substantially along the longitudinal length thereof. A flexible shield device 30 substantially shields a surrounding radial area of the antenna wire 28 from the electric field radially generated therefrom, while permitting a majority of the field to be directed generally in a predetermined direction toward the window portion 27. A flexible insulator 31 is disposed between the shield device 30 and the antenna 28, and defines the window portion 27 enabling the transmission of the directed electric field in the predetermined direction. The antenna 28, the shield device 30 and the insulator 31 are formed for selective manipulative bending thereof, as a unit, to one of a plurality of contact positions to generally conform the window portion 27 to the biological tissue surface 21 to be ablated.

Accordingly, the microwave ablation instrument of the present invention enables manipulative bending of the antenna assembly to conform the window portion to the biological tissue surface to be ablated. This ensures a greater degree of contact between the elongated window portion and the targeted tissue. This is imperative to maintain the radiation efficiency of the antenna, and thus, proper tuning for more efficient microwave transmission. Such manipulative bending also substantially increases the versatility of the instrument since one antenna assembly can be configured to conform to most tissue surfaces.

Briefly, the ablation instrument 20 includes a handle member 23 coupled to the antenna assembly 26 through an elongated tubular shaft or semi-rigid coaxial cable, hereinafter referred to as shaft 32. By manually manipulating the handle, the window portion 27 of the antenna assembly 26 may be oriented and positioned to perform the desired ablation. As mentioned, the shaft 32 is preferably provided a semi-rigid coaxial cable or by a conductive material such as a metallic hypotube which is mounted to the components of the antenna assembly 26 through brazing paste, welding or the like, as will be discussed. Accordingly, when the shaft 32 is provided by the semi-rigid coaxial cable, the braided outer conductor 29 of the semi-rigid coaxial cable 32, peripherally surrounding the center conductor 33, is preferably conductively coupled to the outer conductor of the transmission line 25. Similarly, the inner conductor 33 of the semi-rigid coaxial cable 32 is conductively coupled to the inner conductor of the transmission line 25.

In contrast, when the shaft 32 is provided by the tubular, such as a conductive hypotube, the solid cylindrical shell outer conductor 29 thereof is preferably conductively coupled to the outer conductor of the transmission line 25. In this configuration, the inner conductor and the insulator of the transmission line extend through the cylindrical shell outer conductor 29 of the conductive hypotube 32 to provide the inner conductor 33 thereof. In this manner, the metallic hypotube itself functions as the outer conductor of the transmission line 25 for shielding along the length of the shaft.

Moreover, the shaft 32, whether the hypotube or the semi-rigid coaxial cable, is preferably bendable and malleable in nature to enable shape reconfiguration to position the antenna assembly at a desired orientation relative the handle. This permits the surgeon to appropriately angle the window portion toward the targeted region for tissue ablation. It will be appreciated, however, that the material of the shaft 32 is further sufficiently rigid so that the shaft is not easily deformed during operative use. Such materials for the hypotube, for example, include stainless steel or aluminum having diameters ranging from about 0.090 inches to about 0.200 inches with wall thickness ranging from about 0.010 inches to about 0.050 inches. When the semi-coaxial cable is applied as the shaft 32, the outer diameter of the outer conductor ranges from about 0.090 inches to about 0.200 inches, with wall thickness ranging from about 0.010 inches to about 0.050 inches; while the inner conductor includes a diameter in the range of about 0.010 inches to about 0.050 inches.

The transmission line 25 is typically coaxial, and is coupled to a power supply (not shown) through connector 35 (FIG. 1). As best illustrated in FIGS. 2 and 5-7, the microwave ablation instrument 20 generally includes an elongated antenna wire 28 having a proximal end attached to center conductor 33 of transmission line 25. These linear wire antennas radiate a cylindrical electric field pattern consistent with the length thereof. It will be appreciated, however, that the antenna may be any other configuration, as well, such as a helical or coiled antenna.

The electrical interconnection between the antenna wire 28 and the distal end of the center conductor 33 may be made in any suitable manner such as through soldering, brazing, ultrasonic welding or adhesive bonding. Moreover, the antenna wire 28 may be an extension of the center conductor of the transmission line itself which has the advantage of forming a more rugged connection therebetween. Typically, the antenna wire 28 is composed of any suitable material, such as spring steel, beryllium copper, or silver-plated copper.

As will be discussed in greater detail below, the diameter of the antenna wire may vary to some extent based on the particular application of the instrument. By way of example, an instrument suitable for use in an atrial fibrillation application may have typical diameter in the range of approximately 0.005 to 0.030 inches. More preferably, the diameter of antenna wire may be in the range of approximately 0.013 to 0.020 inches.

The antenna 28 is designed to have a good radiation efficiency and to be electrically balanced. Consequently, the energy delivery efficiency of the antenna is increased, while the reflected microwave power is decreased which in turn reduces the operating temperature of the transmission line. Moreover, the radiated electromagnetic field is substantially constrained from the proximal end to the distal end of the antenna. Thus, the field extends substantially radially perpendicularly to the antenna and is fairly well constrained to the length of the antenna itself regardless of the power used. This arrangement serves to provide better control during ablation. Instruments having specified ablation characteristics can be fabricated by building instruments with different length antennas.

Briefly, the power supply (not shown) includes a microwave generator which may take any conventional form. When using microwave energy for tissue ablation, the optimal frequencies are generally in the neighborhood of the optimal frequency for heating water. By way of example, frequencies in the range of approximately 800 MHz to 6 GHz work well. Currently, the frequencies that are approved by the U.S. Food and Drug Administration for experimental clinical work are 915 MHz and 2.45 GHz. Therefore, a power supply having the capacity to generate microwave energy at frequencies in the neighborhood of 2.45 GHz may be chosen. A conventional magnetron of the type commonly used in microwave ovens is utilized as the generator. It should be appreciated, however, that any other suitable microwave power source could be substituted in its place, and that the explained concepts may be applied at other frequencies like about 434 MHz, 915 MHz or 5.8 GHz (ISM band).

Figure 3:
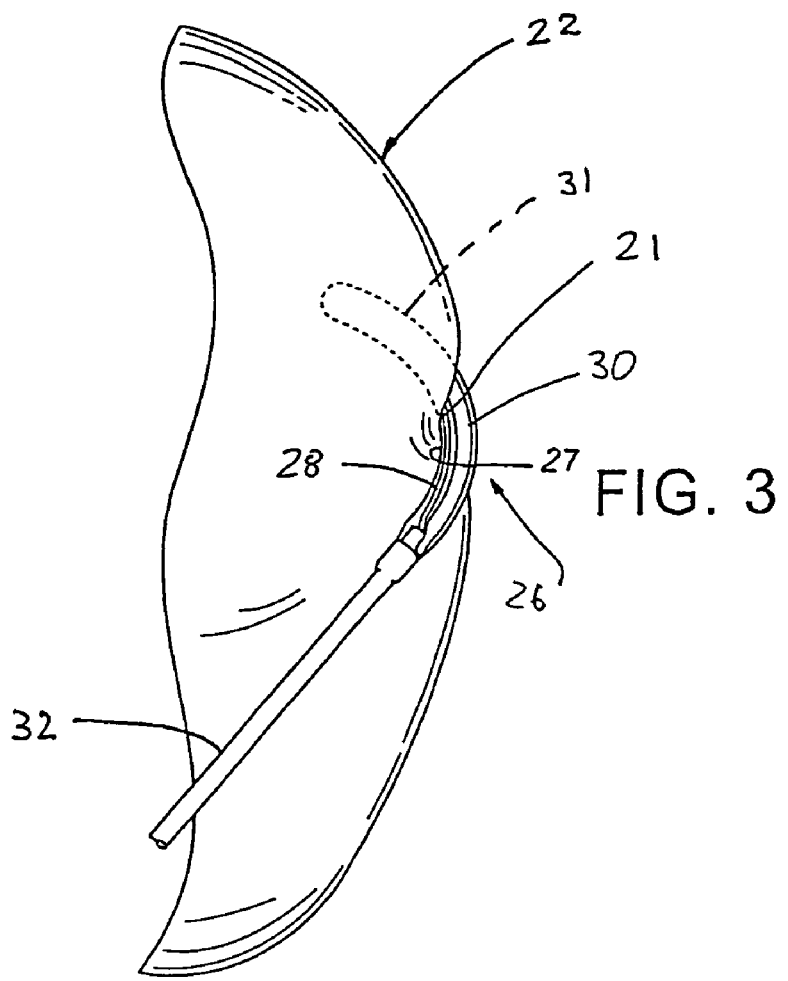
FIG. 3 is an enlarged, fragmentary, top perspective view of the antenna assembly of FIG. 1 illustrated in a bent position to conform to a surface of the tissue to be ablated.
Figure 4:
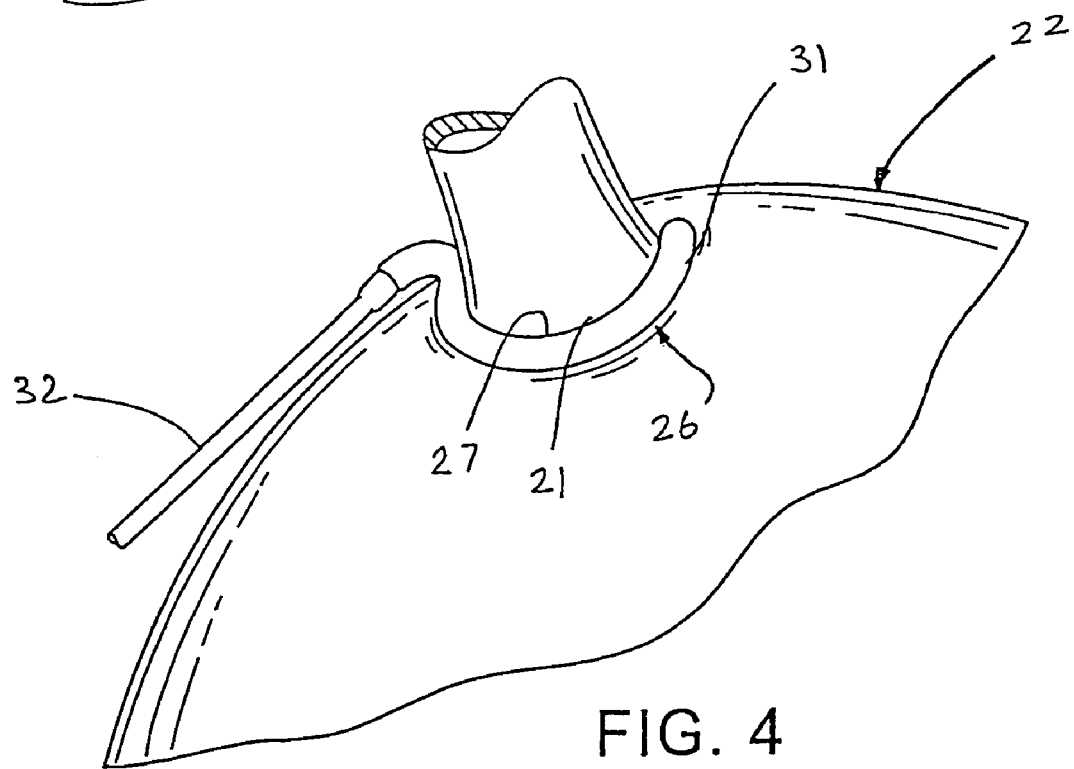
FIG. 4 is an enlarged, fragmentary, top perspective view of the antenna assembly of FIG. 2 illustrated in another bent position to conform to a surface of the tissue to be ablated.

Referring back to FIGS. 1-5, the microwave ablation instrument 20 of the present invention will be described in detail. As above-mentioned, the antenna wire 28, the shield device 30 and the insulator 31 of the antenna assembly cooperate, as a unit, to enable selective manipulative bending thereof to one of a plurality of contact positions to generally conform the window portion 27 to the biological tissue surface 21 to be ablated. Thus, FIGS. 3 and 4 illustrate two particular contact positions where the window portion 27 may be configured to maintain contact for substantially curvilinear tissue surfaces 21. Consequently, due to the proper impedance matching between the medium of the insulator 31 and that of the biological tissue, contact therebetween along the window portion 27 is necessary to maintain the radiation efficiency of the antenna.

Figure 2:
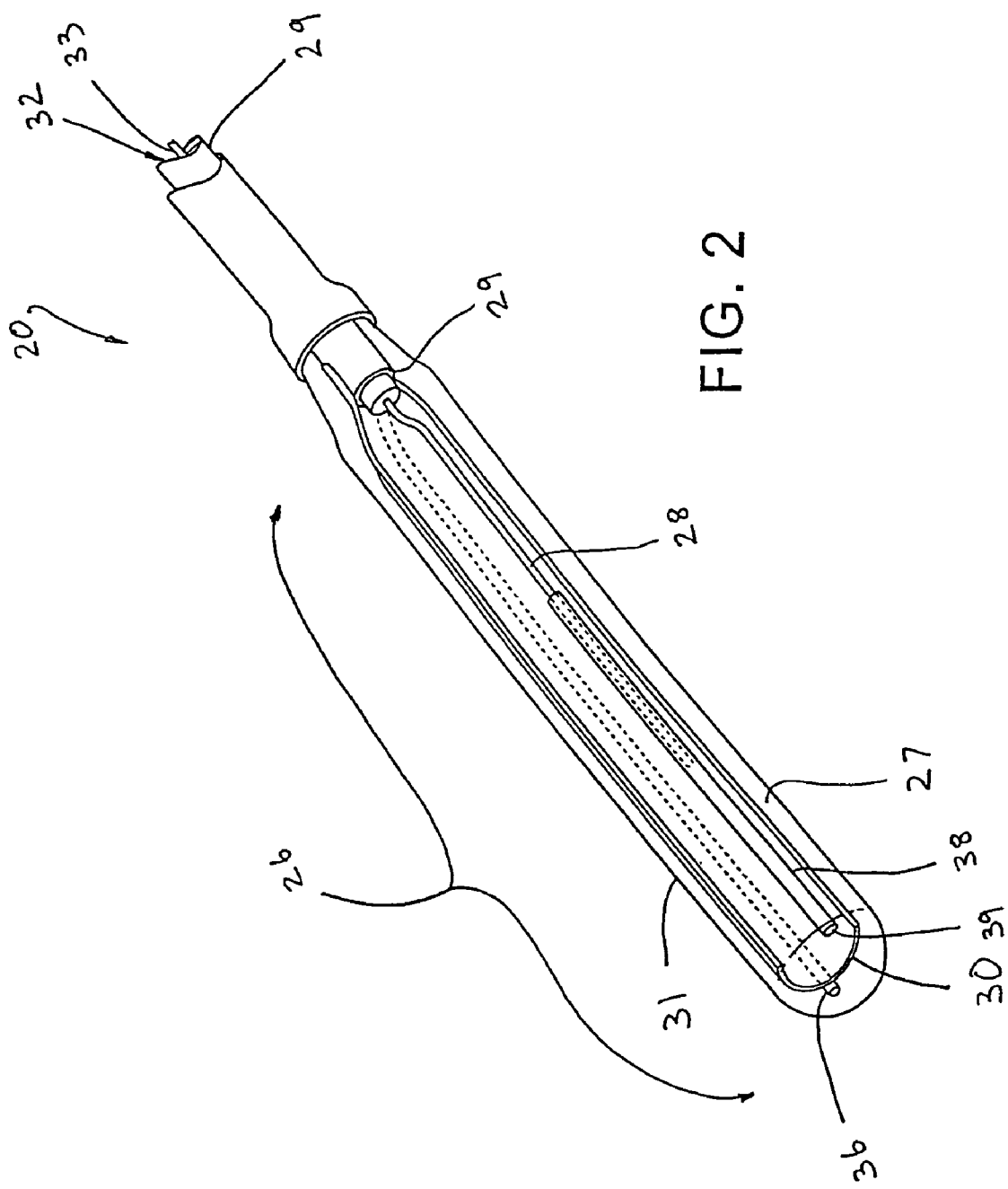
FIG. 2 is an enlarged, fragmentary, top perspective view of the antenna assembly of FIG. 1 mounted to a distal end of a handle member of the ablation instrument.
Figure 5:
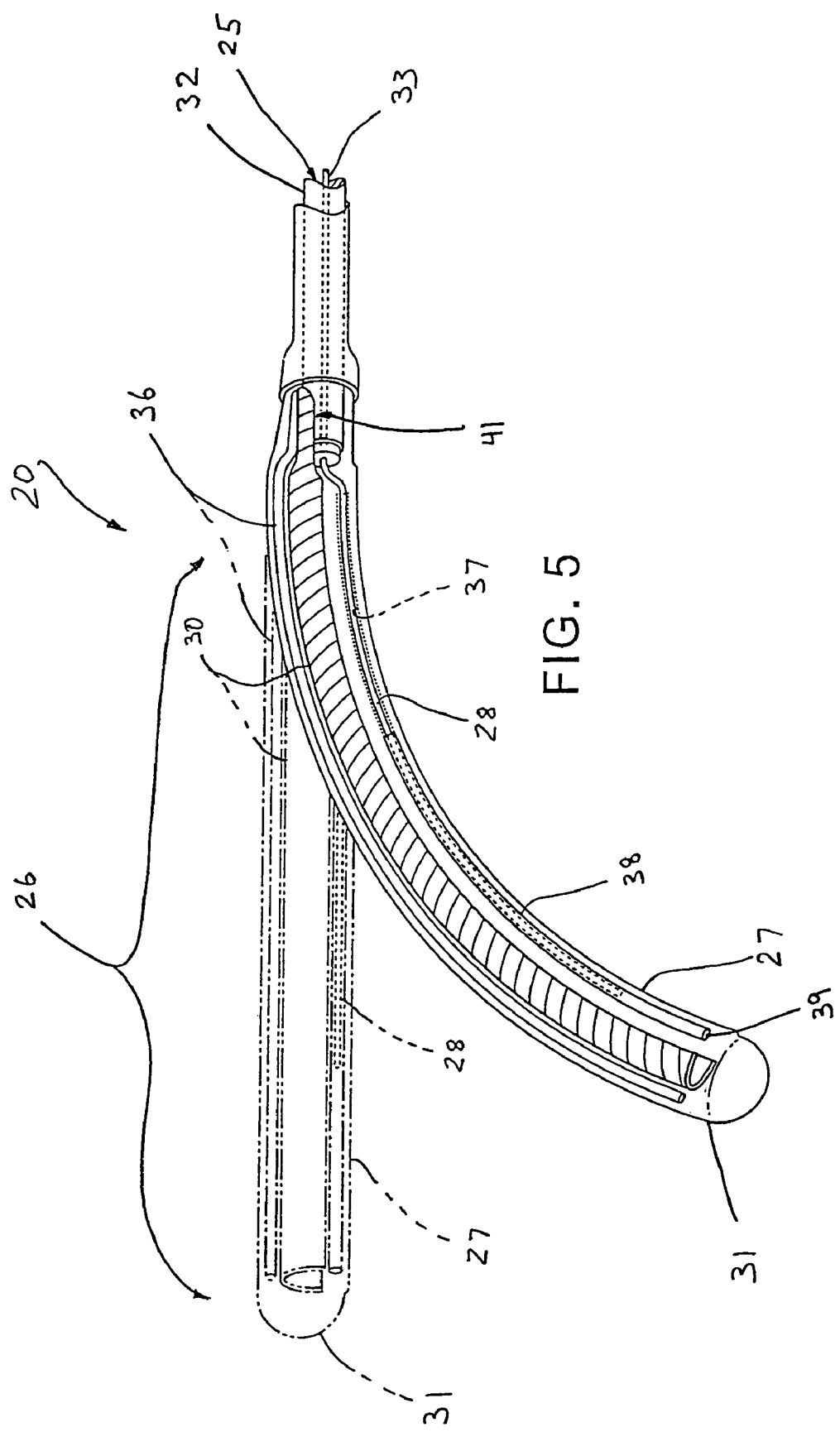
FIG. 5 is an enlarged, fragmentary, top plan view of the antenna assembly of FIG. 2 illustrating movement between a normal position (phantom lines) and a bent position (solid lines).

As above-mentioned, a flexible shield device 30 extend substantially along the length of the antenna substantially parallel to the longitudinal axis of the antenna in a normal unbent position (shown in solid lines in FIG. 2 and phantom lines in FIG. 5). The shield device 30 is formed and dimensioned to shield selected surrounding areas radially about the antenna wire 28 from the electric field radially generated therefrom, while reflecting the field and permitting the passage of the field generally in a predetermined direction toward the strategically located window portion 27 of the insulator 31. As best viewed in FIGS. 2, 7 and 9, the shield device 30 is preferably semi-cylindrical or arcuate-shaped in the transverse cross-sectional dimension to reflect the impinging field back toward the antenna thereof.

Tissue ablation can thus be more strategically controlled, directed and performed without concern for undesirable ablation of other adjacent tissues which may otherwise be within the electromagnetic ablation range radially emanating from the antenna. In other words, any other tissues surrounding the peripheral sides of the antenna which are out of line of the window portion of the cradle will not be subjected to the directed electric field and thus not be ablated. This ablation instrument assembly is particularly suitable for ablation procedures requiring accurate tissue ablations such as those required in the MAZE III procedure above-mentioned.

Briefly, it will be appreciated that the phrase "peripheral area immediately surrounding the antenna" is defined as the immediate radial transmission pattern of the antenna which is within the electromagnetic ablation range thereof when the shield assembly is absent.

The shield device 30 is preferably composed of a high conductivity metal to provide superior microwave reflection. The walls of the shield device 30, therefore, are substantially impenetrable to the passage of microwaves emanating from the antenna 28 to protect a backside of the antenna assembly from microwave exposure. More specifically, when an incident electromagnetic wave originating from the antenna reaches the conductive shield device, a surface current is induced which in turn generates a responsive electromagnetic field that will interfere with that incident field. Consequently, this incident electromagnetic field together with the responsive electromagnetic field within the shield device 30 of the antenna assembly 26 cancel and are thus negligible.

FIGS. 2 and 5 best illustrate that the shield device 30 is preferably provided by a braided conductive mesh having a proximal end conductively mounted to the distal portion of the outer conductor of the coaxial cable. This conductive mesh is preferably thin walled to minimize weight addition to the shield assembly yet provide the appropriate microwave shielding properties, as well as enable substantial flexibility of the shield device during bending movement. One particularly suitable material is stainless steel, for example, having mesh wires with a thickness in the range of about 0.005 inches to about 0.010 inches, and more preferably about 0.007 inches.

As mentioned, an elongated microwave antenna normally emits an electromagnetic field substantially radially perpendicular to the antenna length which is fairly well constrained to the length of the antenna wire regardless of the power used. However, to assure proper shielding, the longitudinal length of the shield may be longer than and extend beyond the distal and proximal ends of the antenna wire 28.

To maintain the electromagnetic field characteristics of the antenna during operative use, even with a flexible antenna, it is important to maintain the position of a transverse cross-sectional segment of shield device 30 relative a corresponding transverse cross-sectional segment of the antenna wire 28. Relative position changes between the segments may alter the radiation pattern and the radiation efficiency of the antenna. Accordingly, to stabilize these transverse cross-sectional segments of the shield device relative to the corresponding transverse cross-sectional segments of the antenna wire 28, the antenna assembly 26 includes the flexible insulator 31 preferably molded over and disposed between the shield device 30 and the antenna wire 28.

The insulator 31 is preferably further molded to the distal portion of the metallic tubular shaft, and is preferably cylindrical shaped having an axis generally coaxial with that of the shield device 30. The insulator 31 further performs the function of decreasing the coupling between the antenna 28 and the flexible shield device 30. Should the antenna 28 be too close to the conductive shield device 30, a strong current may be induced at the surface thereof. This surface current will increase the resistive losses in the metal and the temperature of the cradle device will increase. On the other hand, direct conductive contact or substantially close contact of the antenna with the metallic cradle device will cause the reflective cradle device to become part of the radiative structure, and begin emitting electromagnetic energy in all directions.

The insulator 31 is therefore preferably provided by a good, low-loss dielectric material which is relatively unaffected by microwave exposure, and thus capable of transmission of the electromagnetic field therethrough. Moreover, the insulator material preferably has a low water absorption so that it is not itself heated by the microwaves. Finally, the insulation material must be capable of substantial flexibility without fracturing or breaking. Such materials include moldable TEFLON®, silicone, or polyethylene, polyimide, etc.

In the preferred embodiment, the insulator 31 defines an elongated window portion 27 extending substantially adjacent and parallel to the antenna wire 28. Thus, as shown in FIGS. 5 and 7-9, a longitudinal axis of the antenna wire 28 is off-set from, but parallel to, the longitudinal axis of insulator 31 in a direction toward the window portion. This configuration positions the antenna wire 28 actively in the window portion 27 to maximize exposure of the targeted tissue to the microwaves generated by antenna, as well as further space the antenna sufficiently away from the shield device to prevent the above-mentioned electrical coupling.

In a normal unbent position of the antenna assembly 26 (shown in solid lines in FIG. 2 and phantom lines in FIG. 5), the window portion 27 is substantially planar and rectangular in shape. Upon bending thereof, however, the face of the window portion 27 can be manipulated to generally conform to the surface of the tissue 22 to be ablated. Thus, a greater degree of contact of a curvilinear surface 21 of a tissue 22 with full face of the window portion 27 is enabled. The radiation pattern along the antenna, therefore, will not be adversely changed and the antenna will remain tuned, which increases the efficiency and the penetration depth of the energy delivery into the tissue 22.

In accordance with the present invention, the window portion 27 is strategically sized and located relative the shield device to direct a majority of the electromagnetic field generally in a predetermined direction. As best viewed in FIGS. 2, 5 and 7, the window portion 27 preferably extends longitudinally along the insulator 31 in a direction substantially parallel to the longitudinal axis thereof. The length of the ablative radiation is therefore generally constrained to the length of the antenna wire 28, and may be adjusted by either adjusting the length of the antenna wire 28. To facilitate the coupling between the coaxial cable and the antenna wire, the proximal end of the window portion 27 generally extends proximally a little longer than the proximal end of the antenna 28 (about 2-5 mm). On the distal end, however, the window portion 27 is configured to approximate the length of the distal end of the shield device 30. Incidentally, as will be described in greater detail below, the distal portion of the shield device 30 extends well beyond the distal end of the antenna to accommodate for bending of the antenna assembly 26.

Figure 9:
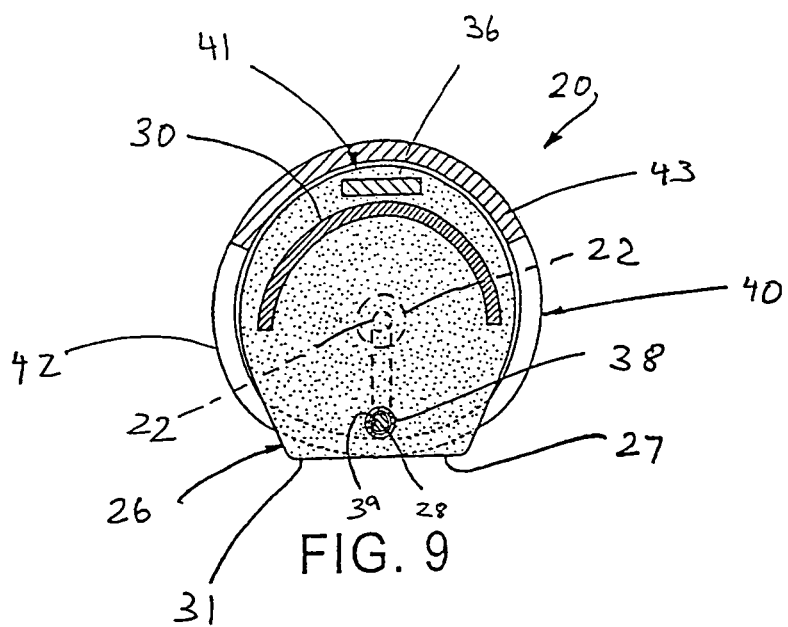
FIG. 9 is an enlarged, front elevation view, in cross-section, of the antenna assembly taken substantially along the plane of the line 9-9 in FIG. 8.

FIGS. 7 and 9 best illustrate that the radiation pattern of the electromagnetic field delivered from the window portion 27 may extend radially from about 120° to about 180°, and most preferably extend radially about 180°, relative the longitudinal axis of the insulator. Thus, a substantial portion of the backside of the antenna is shielded from ablative exposure of the microwaves radially generated by the antenna in directions substantially perpendicular to the longitudinal axis thereof. The circumferential dimension of window portion 27, hence, may vary according to the breadth of the desired ablative exposure without departing from the true spirit and nature of the present invention. Moreover, while a small percentage of the electromagnetic field, unshielded by the shield device, may be transmitted out of other non-window portions of the insulator, a substantial majority will be transmitted through the window portion. This is due to the impedance matching characteristics which are turned to contact between the tissue and the window portion.

Accordingly, the predetermined direction of the ablative electromagnetic field radially generated from the antenna may be substantially controlled by the circumferential opening dimension, the length and the shape of the window portion 27. Manipulating the shape of the antenna assembly 26 to conform the window portion generally to the shape of the targeted tissue surface, and positioning of window portion 27 in the desired direction for contact with the tissue, thus, controls the direction of the tissue ablation without subjecting the remaining peripheral area immediately surrounding the antenna to the ablative electromagnetic field.

In a preferred embodiment of the present invention, an elongated, bendable, retaining member, generally designated 36, is provided which is adapted for longitudinal coupling therealong to the insulator 31. Once the window portion 27 is manually manipulated for conformance to the biological tissue surface to be ablated, this bendable retaining member 36 functions to retain the insulator 31 in the one position for operative ablation thereof. As best viewed in FIGS. 2, 5 and 7, the retaining member 36 is preferably positioned behind the shield device 30 so as to be shielded from exposure to the microwaves transmitted by antenna 28. The retaining member preferably extends along the full length of the shield device in a direction substantially parallel to the longitudinal axis of the insulator 31.

This retaining member 36 must be a ductile or bendable material, yet provide sufficient rigidity after being bent, to resist the resiliency of the insulator to move from a bent position (e.g., FIGS. 3 and 4) back toward the normal position (FIG. 2). Moreover, both the retaining member 36 and the antenna wire 28 must not be composed of a material too rigid or brittle as to fracture or easily fatigue tear during repeated bending movement. Such materials for the retaining member include tin or silver plated copper or brass, having a diameter in the range of about 0.020 inch to about 0.050 inches.

In a preferred form, retaining member 36 is molded or embedded in the moldable insulator. This facilitates protection of the retaining member 36 from contact with corrosive elements during use. It will be appreciated, however, that retaining member 36 could be coupled to the exterior of the insulator longitudinally therealong.

As shown in FIGS. 2 and 5, a proximal portion of the retaining member 36 is positioned adjacent and substantially parallel to a distal portion of the shaft 32. Preferably, the proximal portion of the retaining member 36 is rigidly affixed to the distal portion of the shaft 32 at a coupling portion 41 thereof to provide relative stability between the shaft and the antenna assembly 26 during bending movement. While such rigid attachment is preferably performed through soldering, brazing, or ultrasonic welding, the coupling could be provided by a rigid, non-conductive adhesive or the like.

Preferably, the retaining member 36 is cylindrical-shaped, having a substantially uniform transverse cross-sectional dimension. It will be appreciated, however, that other geometric transverse cross-sectional dimensions may apply such as a rectangular cross-section. As shown in FIG. 9, this retaining member 36 is in the form of a thin metallic strip embedded atop the shield device 30. In this configuration, due to the relative orientation of the antenna and the shield device 30 bending in vertical direction, will be permitted while movement in a lateral side-to-side direction will be resisted. Moreover, the retaining member 36 may not be uniform in transverse cross-sectional dimension to permit varied rigidity, and thus variable bending characteristics, longitudinally along the antenna assembly.

In another alternative configuration, the retaining member 36 may be incorporated into the shield device or the antenna itself. In either of these configurations, or a combination thereof, the shield device and/or the antenna must provide sufficient rigidity to resist the resiliency of the insulator 31 to move from the bent position (e.g., FIGS. 3 and 4) back toward the normal position (FIG. 2).

In accordance with the present invention, the insulator 31 defines a receiving passage 37 formed for sliding receipt of the antenna wire 28 longitudinally therein during manipulative bending of the antenna assembly 26. As best viewed in FIGS. 5 and 6, this sliding reciprocation enables bending of the antenna assembly 26 without subjecting the antenna 28 to compression or distension during bending movement of the antenna which may ultimately fatigue or damage the antenna, or adversely alter the integrity of the electromagnetic field.

Such displacement is caused by the bending movement of the antenna assembly pivotally about the retaining member 36. For example, as shown in FIG. 7, during concave bending movement (FIGS. 2 and 5) or convex bending movement (FIG. 8) of the window portion 27 of the antenna assembly 26, the pivotal or bending movement will occur about the longitudinal axis of the retaining member 36. Accordingly, upon concave bending movement of the window portion 27 (FIGS. 2 and 5), the length of the receiving passage 37 shortens. This is due to the fact that the insulator 31 compresses at this portion thereof since the receiving passage 37 is positioned along the radial interior of the retaining member. Essentially, the radius of curvature of the receiving passage 37 is now less than the radius of curvature of the outer retaining member 36. However, the longitudinal length of the antenna 28 slideably retained in the receiving passage 37 will remain constant and thus slide distally into the receiving passage.

In contrast, upon convex bending movement of the window portion 27 (FIG. 8), the length of the receiving passage 37 distends since the receiving passage 37 will be positioned on the radial exterior of the retaining member 36. In this situation, the radius of curvature of the receiving passage 37 will now be greater than the radius of curvature of the outer retaining member 36. Consequently, the distal end of the antenna slides proximally in the receiving passage 37.

Preferably, the diameter of the receiving passage is about 5% to about 10% larger than that of the antenna wire 28. This assure uninterfered sliding reciprocation therein during bending movement of the antenna assembly 26. Moreover, the proximal end of the receiving passage 37 need not commence at the proximal end of the antenna wire 28. For instance, since the displacement at the proximal portion of the antenna wire 28 is substantially less than the displacement of the antenna wire 28 at a distal portion thereof, the proximal end of the receiving passage 37 may commence about 30% to about 80% from the proximal end of the antenna wire 28. The distal end of the receiving passage 37, on the other hand, preferably extends about 30% to about 40% past the distal end of the antenna wire 28 when the antenna assembly is in the normal unbent position. As above-indicated, this space in the receiving passage 37 beyond the distal end of the antenna 28 enables reciprocal displacement thereof during concave bending movement.

To assure that the distal end of the antenna 28 does not pierce through the relatively soft, flexible insulating material of the insulator 31, during bending movement, the tip portion thereof may be rounded or blunted. In another configuration, the receiving passage 37 may be completely or partially lined with a flexible tube device 38 (FIGS. 2 and 5-7) having a bore 39 formed and dimensioned for sliding longitudinal reciprocation of the antenna distal end therein. The walls of tube device 38 are preferably relatively thin for substantial flexibility thereof, yet provide substantially more resistance to piercing by the distal end of the antenna 28. Moreover, the material composition of the tube device must have a low loss-tangent and low water absorption so that it is not itself affected by exposure to the microwaves. Such materials include moldable TEFLON® and polyimide, polyethylene, etc.

Figure 8:
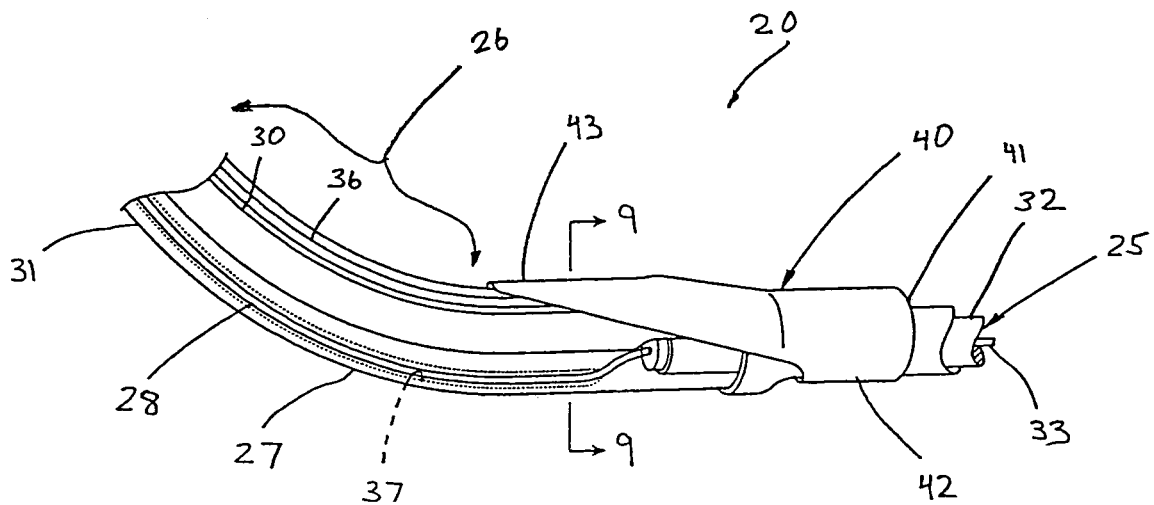
FIG. 8 is an enlarged, fragmentary, side elevation view of the antenna assembly of FIG. 2 having a restraining sleeve coupled thereto.

Referring now to FIGS. 8 and 9, a restraining sleeve, generally designated 40, is provided which substantially prevents convex bending movement of the retaining member 36 at the proximal portion thereof. At this coupling portion 41, where the retaining member 36 and the shield device 30 are mounted to the distal portion of the shaft 32, repeated reciprocal bending in the convex direction may cause substantial fatigue of the bond, and ultimately fracture. The restraining sleeve 40, thus, preferably extends longitudinally over the coupling portion 41 to maintain the integrity of the coupling by preventing strains thereon. Essentially, such convex bending movement will then commence at a portion of the antenna assembly 26 distal to the coupling portion.

The restraining sleeve 40 includes an arcuate shaped base portion 42 removably mounted to and substantially conforming with the circumferential cross-sectional dimension of the proximal portion of the insulator 31 (FIG. 9). The base portion 42 is rigidly affixed to the antenna assembly and/or the shaft to provide protective stability over the coupling portion 41.

A finger portion 43 extends distally from the base portion 42 in a manner delaying the commencement of convex bending of the antenna assembly to a position past the distal end of the finger portion 43. Consequently, any strain upon the coupling portion 41 caused by convex bending movement of the antenna assembly is eliminated.

Figure 10:
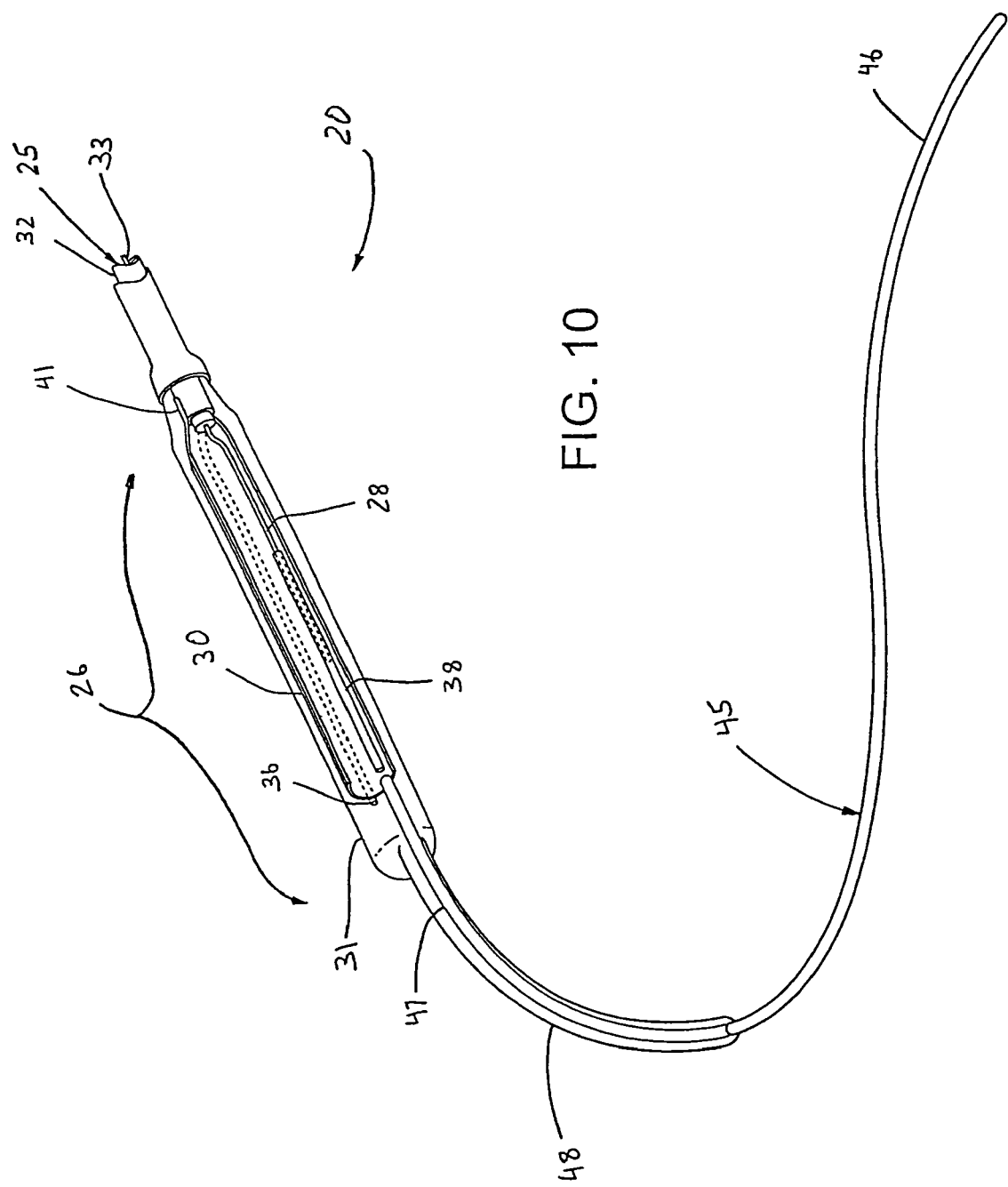
FIG. 10 is a diagrammatic top plan view of an alternative embodiment microwave ablation instrument system constructed in accordance with one embodiment of the present invention.
Figure 11:
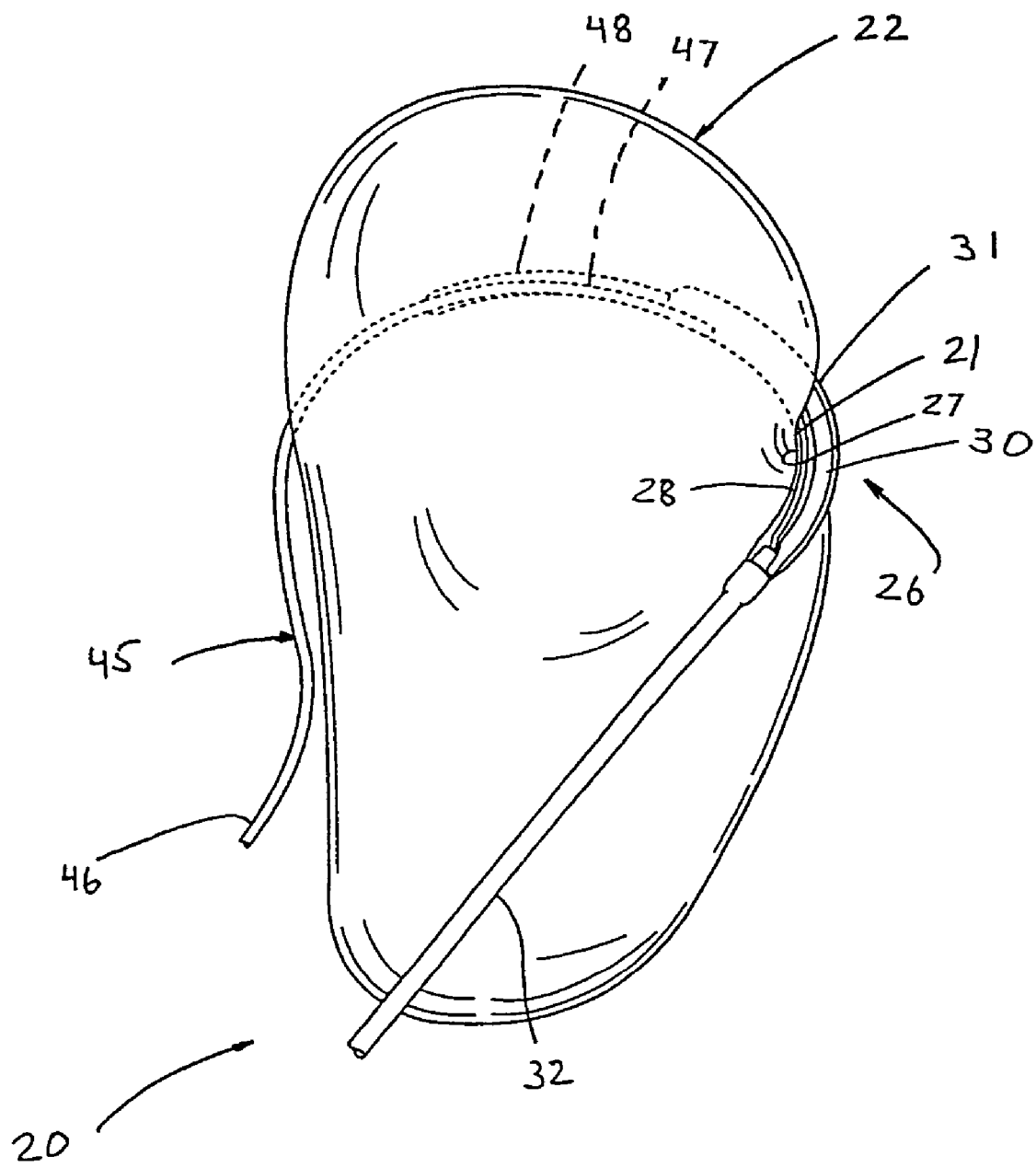
FIG. 11 is a reduced, fragmentary, top perspective view of the antenna assembly of FIG. 10 illustrated in a bent position to conform to a surface of the tissue to be ablated.

In another embodiment of the present invention, the microwave ablation instrument 20 includes an elongated grip member 45 having a distal grip portion 46 and an opposite proximal portion 47 coupled to a distal portion of the antenna assembly 26. As best illustrated in FIGS. 10 and 11, the grip member 45 and the handle member 23 of the ablation instrument 20 cooperates to selectively bend the flexible antenna assembly 26 and selectively urge the window portion 27 into abutting contact with the biological tissue surface to be ablated. For example, this application is particularly useful when the targeted tissue surface is located at a rear portion of an organ or the like. FIG. 11 illustrates that, during open procedures, the elongated grip member 45 may be passed around the backside of the organ until the window portion 27 of the antenna assembly is moved into abutting contact with the targeted tissue surface 21. Subsequently, the handle member 23 at one end of the ablation instrument, and the grip member 45 at the other end thereof are manually gripped and manipulated to urge the window portion 27 into ablative contact with the targeted tissue surface.

This configuration is beneficial in that the window portion 27 is adapted to conform to the tissue surface upon manual pulling of the grip member 45 and the handle member 23. As the flexible antenna assembly 26 contacts the targeted tissue 22, the window portion 27 thereof is caused to conform to the periphery of the tissue surface. Continued manipulation of the grip member 45 and the handle member 23 further urge bending contact. Accordingly, this embodiment will not require a retaining member for shape retention.

The elongated grip member 45 is provided by a substantially flexible rod having a diameter smaller than the diameter of the insulator 31. Such flexibility enables manipulation of the rod to position its distal end behind a targeted biological tissue 22. Once the distal grip portion 46 of the grip member 45 is strung underneath organ 22 or the like, the distal grip portion 46 may be gripped to pull the antenna assembly 26 behind the organ 22 for ablation of the targeted tissue.

It will be appreciated, however, that the rod 45 should not be substantially more flexible than that of the antenna assembly. This assures that the window portion 27 of the insulator 31 will be caused to conform to the curvilinear surface of the targeted tissue 22, as opposed to the mere bending of the flexible rod 45. Such materials for the flexible rod 45 includes Pebax filled with silicone and polyethylene, polyurethane, etc.

To mount flexible rod 48 to the ablation instrument 20, the antenna assembly 26 includes a mounting portion 48 extending distally from the insulator 31. This mounting portion 48 is preferably integrally formed with the insulator 31 and is of a sufficient length to enable the proximal portion of flexible rod 45 to be integrally molded thereto without interference with the shield device 30 and/or the antenna wire 28.

In the preferred embodiment, a longitudinal axis of the flexible rod 45 is off-set from the longitudinal axis of the insulator 31 in the direction toward the window portion 27. As viewed in FIG. 11, this off-set preferably positions the longitudinal axis of the flexible rod proximately in co-axial alignment with the antenna. This arrangement facilitates alignment of the window portion 27 against the targeted tissue 22 as the grip member 45 and the handle member 23 are manipulated to conform the window portion 27 with and against the tissue surface 21. Due to the off-set nature of the flexible rod 45, when the antenna assembly and the rod are tightened around the biological tissue 22, the antenna assembly 26 is caused to rotate about its longitudinal axis toward an orientation of least resistance (i.e., a position where the flexible rod 45 is closest to the biological tissue 22).

Additionally, as shown in FIG. 12, the handle member 23 may be elongated and substantially flexible in a manner similar to the elongated grip member 45. In another embodiment of the present invention, the handle member 23 includes a proximal grip portion 50 and an opposite distal portion 51 coupled to a proximal portion of the antenna assembly 26. Thus, the flexible handle member 23 and the flexible grip member 45 cooperate to selectively bend the flexible antenna assembly 26 and selectively urge the window portion 27 into abutting contact with the biological tissue surface to be ablated. As another example, this application is particularly useful for creating long continuous linear lesions (E.g., to enclose the pulmonary veins when treating atrial fibrillation or the like). The flexible handle member 23 at one end of the ablation instrument, and the flexible grip member 45 at the other end thereof are manually gripped and manipulated to urge the window portion 27 into ablative contact with the targeted tissue surface. This can be performed by simply sliding the antenna assembly 26 by pulling either the flexible grip member 45 or the flexible handle member 23 to position the widow portion 27 against the tissue. Moreover, this can be used to slightly overlap the lesions to generate a long continuous lesion without gaps easily end the targeted tissue surface is located at a rear portion of an organ or the like.

The elongated flexible handle member 23 is preferably provided by a substantially flexible coaxial cable appropriately coupled to the transmission line. In some instances, the handle member 23 may simply be an extension of the transmission line.

Preferably, the flexible coaxial cable handle member 23 is covered by a plastic sleeve such as Pebax, PE Polyolifin, etc. Such dual flexibility enables increased manipulation of both the gripping member and the handle member. To mount flexible handle member 23 to the antenna assembly 26, the distal portion thereof is preferably integrally formed with the insulator.

Similar to the gripping member 45, a longitudinal axis of the flexible handle member 23 is off-set from the longitudinal axis of the insulator 31 in the direction toward the window portion 27. As viewed in FIG. 12, this off-set, together with the same off-set of the gripping member, preferably positions the longitudinal axis of the handle member proximately in co-axial alignment with the antenna. This arrangement facilitates alignment of the window portion 27 against the targeted tissue 22 as the grip member 45 and the handle member 23 are manipulated to conform the window portion 27 with and against the tissue surface 21. Due to the off-set nature of the flexible rod 45, when the antenna assembly and the rod are tightened around the biological tissue 22, the antenna assembly 26 is caused to rotate about its longitudinal axis toward an orientation of least resistance (i.e., a position where the flexible rod 45 is closest to the biological tissue 22).

In still another aspect of the present invention, a method is provided for treatment of a heart including providing a microwave ablation instrument 20 having a flexible antenna assembly 26 defining a window portion 27 enabling the transmission of a directed electric field therethrough in a predetermined direction. By selectively bending the flexible antenna assembly 26 to one of a plurality of contact positions, the window portion 27 can be generally conformed to the shape of the targeted biological tissue 22 surface to be ablated. The method further includes manipulating the ablation instrument 20 to strategically position the conformed window portion 27 into contact with the targeted biological tissue surface 21; and generating the electric field sufficiently strong to cause tissue ablation to the targeted biological tissue surface 21.

More preferably, this method is directed toward medically refractory atrial fibrillation of the heart. By repeating the bending, manipulating and generating events, a plurality of strategically positioned ablation lesions can be accurately formed in the heart. Collectively, these lesions are formed to create a predetermined conduction pathway between a sinoatrial node and an atrioventricular node of the heart, or to divide the left and/or right atrium in order to avoid any reentry circuits.

These techniques may be preformed while the heart remains beating, such as in a minimally invasive heart procedure, while the heart is temporarily arrested, such as when the heart is stabilized for about 20 or 30 seconds during a cabbage procedure, or while the heart is arrested, such as in an open heart surgery. Moreover, these procedures may be applied to ablate the endocardium as well as the epicardium in order to treat atrial fibrillation throughout the bending, manipulating and generating events. Moreover, the repeated events of bending, manipulating and generating are applied in a manner isolating the pulmonary veins from the epicardium of the heart.

Although only a few embodiments of the present inventions have been described in detail, it should be understood that the present inventions may be embodied in many other specific forms without departing from the spirit or scope of the inventions. Particularly, the invention has been described in terms of a microwave ablation instrument for cardiac applications, however, it should be appreciated that the described small diameter microwave ablation instrument could be used for a wide variety of non-cardiac ablation applications as well.

It should also be appreciated that the microwave antenna need not be a linear antenna. The concepts of the present invention may be applied to any kind of radiative structure, such as a helical dipole antenna, a printed antenna, a slow wave antenna, a lossy transmission antenna or the like. Furthermore, it should be appreciated that the transmission line does not absolutely have to be a coaxial cable. For example, the transmission line may be provided by a stripline, a microstrip line, a coplanar line, or the like.

The invention claimed is:

1. An ablation device for forming a lesion in targeted biological tissue, the device comprising:
   an ablation portion for delivering ablation energy to targeted biological tissue through a window portion in a surface of the ablation portion;
   a handle portion extending proximally of the ablation portion; and
   a grip portion attached to and extending distally from a distal end of the ablation portion is axially offset in a direction toward the window portion to facilitate rotational or translational manipulation of the ablation portion into position relative to the targeted biological tissue.

2. The ablation device according to claim 1 in which the ablation portion and grip portion have similar flexibility.

3. The ablation device according to claim 1 in which the ablation portion includes a high frequency antenna structure disposed therein offset toward the window portion to orient the antenna structure toward biological tissue in position adjacent the window portion.

* * * * *

UNITED STATES PATENT AND TRADEMARK OFFICE
CERTIFICATE OF CORRECTION

| | |
|---|---|
| PATENT NO. | : 7,301,131 B2 |
| APPLICATION NO. | : 11/356917 |
| DATED | : November 27, 2007 |
| INVENTOR(S) | : Jules Gauthier |

It is certified that error appears in the above-identified patent and that said Letters Patent is hereby corrected as shown below:

On the Title Page Item -56-
On page two, under "U.S. PATENT DOCUMENTS," please add:

| | | |
|---|---|---|
| --US-4,601,296 | 07-22-1986 | YERUSHALMI |
| US-4,611,604 | 09-16-1986 | BOTVIDSSON ET AL. |
| US-4,641,649 | 02-10-1987 | WALINSKY ET AL.-- |

On the Title Page Item -56-
On page four, still under "U.S. PATENT DOCUMENTS," please add:

| | | |
|---|---|---|
| --US-6,012,457 | 01-11-2000 | LESH |
| US-6,016,811 | 01-25-2000 | KNOPP ET AL. |
| US-6,016,848 | 01-25-2000 | EGRES, JR. |
| US 6,024,740 | 02-15-2000 | LESH ET AL. |
| US 6,433,464 B2 | 08-13-2002 | JONES |
| US 6,454,758 B1 | 09-24-2002 | THOMPSON ET AL. |
| US 6,461,314 B1 | 10-08-2002 | PANT ET AL. |
| US 6,464,700 B1 | 10-15-2002 | KOBLISH ET AL.-- |

On the Title Page Item -56-
Page 5, under "FOREIGN PATENT DOCUMENTS" please add:

| | | |
|---|---|---|
| --EP 0655 225 B1 | 03-08-2000 | CORDIS EUROPA N.V.-- | and change: "WO 93/02204" to --WO 94/02204--.

UNITED STATES PATENT AND TRADEMARK OFFICE
CERTIFICATE OF CORRECTION

PATENT NO. : 7,301,131 B2 Page 2 of 2
APPLICATION NO. : 11/356917
DATED : November 27, 2007
INVENTOR(S) : Jules Gauthier It is certified that error appears in the above-identified patent and that said Letters Patent is hereby corrected as shown below:

On the Title Page Item -56-
On page 6, "OTHER PUBLICATIONS," please add:

--"Biopsy Needles Liver, Kidney and Soft Tissue Biopsy Menghini Technique Aspirating
Needle Set," Popper & Sons, Inc., Biomedical Instrument Division
DURNEY et al., "Antennas for Medical Applications," Chapter 24, pp. 2, 27-29, Vol. 58.--

In Column 16, please revise line 63, as follows;

--the antenna structure toward targeted biological tissue in position--

Signed and Sealed this

Thirteenth Day of May, 2008

JON W. DUDAS
*Director of the United States Patent and Trademark Office*